(12) United States Patent
Broughton et al.

(10) Patent No.: US 7,288,543 B2
(45) Date of Patent: Oct. 30, 2007

(54) OPIOID RECEPTOR ANTAGONISTS

(75) Inventors: Howard Barff Broughton, Madrid (ES); Nuria Diaz Buezo, Madrid (ES); Charles Howard Mitch, Columbus, IN (US); Concepcion Pedregal-Tercero, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/598,690

(22) PCT Filed: Mar. 8, 2005

(86) PCT No.: PCT/US2005/007052

§ 371 (c)(1),
(2), (4) Date: Sep. 8, 2006

(87) PCT Pub. No.: WO2005/090337

PCT Pub. Date: Sep. 29, 2005

(65) Prior Publication Data

US 2007/0179129 A1    Aug. 2, 2007

(30) Foreign Application Priority Data

Mar. 12, 2004   (EP) ................... 04380057

(51) Int. Cl.
*A01N 43/58* (2006.01)
*A01N 43/54* (2006.01)
*A61K 31/335* (2006.01)
*C07D 239/00* (2006.01)
*C07D 491/00* (2006.01)

(52) U.S. Cl. .............. 514/250; 514/248; 514/267; 514/450; 514/454; 514/468; 514/291; 514/293; 544/234; 544/250; 544/251; 546/89; 546/83; 549/354; 549/359; 549/460; 549/461

(58) Field of Classification Search ........... 544/234, 544/250, 251; 546/89, 83; 549/354, 359, 549/460, 461; 514/250, 248, 267, 450, 293, 514/291, 454, 468
See application file for complete search history.

(56) References Cited

U.S. PATENT DOCUMENTS

| 4,678,779 A | 7/1987 | Meyers et al. |
| 5,532,266 A | 7/1996 | Gottschlich et al. |

FOREIGN PATENT DOCUMENTS

| WO | WO 2004/026305 | 4/2004 |
| WO | WO 2004/080968 | 9/2004 |
| WO | WO 2004/080996 | 9/2004 |
| WO | WO 2005/061442 | 7/2005 |
| WO | WO 2005/066164 | 7/2005 |

OTHER PUBLICATIONS

Brendle et al., antimicrobial agents and chemotherapy, 2002, vol. 46, pp. 797-807.*

* cited by examiner

*Primary Examiner*—Margaret D. Seaman
*Assistant Examiner*—Niloofar Rahmani
(74) *Attorney, Agent, or Firm*—John C. Demeter; Francis O. Ginah

(57) ABSTRACT

A compound of the formula (I) (I) wherein the variables X1 to X6, Ra, Rb, R1 to R7 including R3', E, p, j, y, z, A, B and C are as described or a pharmaceutically acceptable salt, solvate, enantiomer, racemate, diastereomer or mixtures thereof, useful for the treatment, prevention or amelioration of obesity and Related Diseases is disclosed (I)

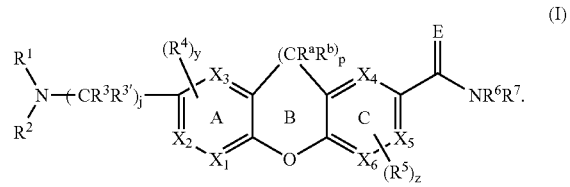

14 Claims, No Drawings

OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure

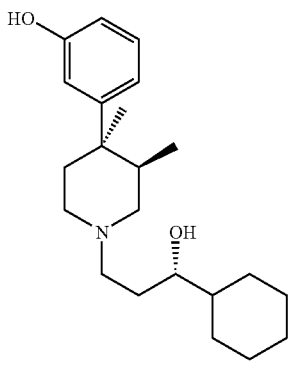

U.S. Pat. No. 6,140,352 discloses the compound of formula

Formula 1

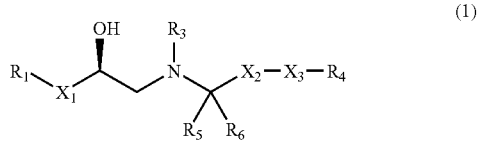

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

Regardless of these and other disclosures of compounds useful as opioid receptor antagonists, or useful for the treatment of obesity, and/or diabetes by other mechanisms, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula (I)

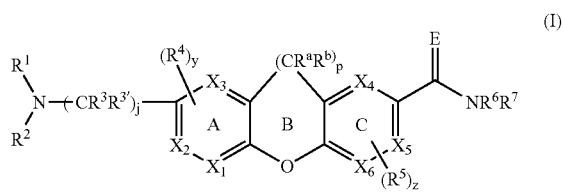

j is 1 or 2;
y is 0, 1, or 2; and z is 0, 1, or 2;
p is 0, 1, or 2;
wherein E is O or NH; and wherein each of
$X_1$, $X_2$, $X_3$, $X_4$, $X_5$, or $X_6$, is C, CH, or N; provided that each of rings A or C has no more than 2 nitrogen atoms; and provided that Ring B has 0 or 1 double bond excluding tautomeric bonds from rings A and C;
$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, $C(O)C_1$-$C_8$ alkyl, $SO_2C_1$-$C_8$alkyl, $SO_2C_1$-$C_8$alkylNR$^8$R$^8$, $(CH_2)_nC(O)NR^8R^8$, $SO_2C_1$-$C_{10}$ alkylaryl, $SO_2C_1$-$C_8$alkylheterocyclic, $C_4$-$C_{10}$ alkylcycloalkane, $(CH_2)_nC(O)OR^8$, and $(CH_2)_nC(O)R^8$; wherein each of the alkyl, alkenyl, and aryl groups are optionally substituted with one to five groups independently selected from $C_1$-$C_8$ alkyl, $C_2$-$C_8$ alkenyl, phenyl, $C_3$-$C_8$ cycloalkyl, $C_1$-$C_8$ alkylaryl, and $C(O)C_1$-$C_8$ alkyl; and wherein $R^1$ and $R^2$ may optionally combine with each other to form a 4, 5, 6, or 7-membered nitrogen-containing heterocycle which nitrogen—containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $CO(O)C_1$-$C_8$ alkyl, halo, $C_1$-$C_8$ haloalkyl;
$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^a$ and $R^b$ are each independently selected from hydrogen, and $C_1$-$C_3$ alkyl or combine with their respective carbon atoms to form the vinyl diradical —CH=CH—;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_m NSO_2C_1$-$C_8$ alkyl, $(CH_2)_m NSO_2$phenyl, $(CH_2)_m NSO_2$aryl, —$C(O)C_1$-$C_8$ alkyl, and —$C(O)OC_1$-$C_8$ alkyl; wherein each $R^4$ and $R^5$ is attached to its respective ring only at carbon atoms; wherein m is 1 or 2; and n is 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, $SO_2C_1$-$C_8$ alkyl, $SO_2C_1$-$C_8$ alkylaryl, $SO_2C_1$-$C_8$ alkylheterocyclic, aryl, $C_1$-$C_8$ alkylaryl, $C_3$-$C_7$ cycloalkane, $C_1$-$C_6$ alkylcycloalkane, $(CH_2)_n C(O)OR^8$, $(CH_2)_n C(O)R^8$, $(CH_2)_m C(O)NR^8R^8$, and $(CH_2)_m NSO_2R^8$; wherein each of the alkyl, alkenyl, and aryl groups are optionally substituted with one to five groups independently selected from $C_1$-$C_8$ alkyl, $C_2$-$C_8$ alkenyl, phenyl, and $C_1$-$C_8$ alkylaryl; and wherein $R^6$ and $R^7$ may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl; or a pharmaceutically acceptable salt, solvate, prodrug, tautomers, enantiomer, racemate, diastereomer, or mixture of diastereomers thereof.

The present invention also provides a method for the prevention, treatment and/or amelioration of the symptoms of obesity and Related Diseases comprising administering a therapeutically effective amount of a compound of formula (I) or a pharmaceutically acceptable salt, solvate, enantiomer, racemate, diastereomer or mixture of diastereomers thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or a pharmaceutically acceptable salt, solvate, enantiomer, racemate, diastereomer or mixture of diastereomers thereof.

The present invention relates to a compound of formula (I) useful for the manufacture of a medicament for the treatment, prevention and/or amelioration of symptoms associated with obesity and Related Diseases.

In another embodiment, the present invention relates to a compound of formula I or a pharmaceutically acceptable salt, solvate, racemate, enantiomer, diastereomer or mixture thereof, useful as an appetite suppressant.

The present invention relates to a method of achieving weight loss while maintaining lean muscle mass or minimizing the loss of lean muscle mass comprising administering a compound of formula I or a pharmaceutically acceptable salt, solvate, enantiomer, racemate, diastereomer or mixture thereof, to a patient in need thereof.

The present invention provides a compound of formula I useful singly or in combination with other agents approved for the treatment, prevention and/or amelioration of obesity and related diseases and symptoms thereof.

DETAILED DESCRIPTION OF THE INVENTION

As used herein, the term "patient" includes human and non-human animals such as companion animals (dogs and cats and the like) and livestock animals.

The preferred patient of treatment, amelioration and/or prevention of obesity and Related Diseases is a human.

The terms "treating" and "treat", as used herein, include their generally accepted meanings e.g. preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of obesity and Related Diseases and the symptoms associated therewith, in a patient afflicted with same or reducing the likelihood that the recipient of a compound of formula I will be afflicted with or develop any of the pathological conditions or sequela thereof described herein.

As used herein, the term "effective amount" is synonymous with "effective dose" and means an amount of a compound of formula I that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of a compounds of formula I or a combination of a compound of formula I and a co-antagonist of the opioid receptor or a combination a compound of formula I and other effective anti-obesity, weight loss or antidiabetic agent.

The term "formulation", as in pharmaceutical formulation, or "pharmaceutical composition" is intended to encompass a product comprising the Active Ingredient (as defined supra), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompasses a compound of the formula I and a pharmaceutically acceptable co-antagonist of opioid receptors useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia.

As used herein "other agents" approved for the treatment of obesity and/or related disease, or useful for weight loss and/or appetite suppression include but are not limited to Xenical®, Meridia®, Lipitor®, Crestor®, Pravachol®, Zetia®, cannabinoid receptor antagonists, and other opioid receptor antagonists.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds. A nitrogen containing heterocycle may be attached to or fused to an existing ring substituent thus forming a bicyclic or tricyclic ring system. Nonetheless, the direct result of the formation of a nitrogen containing heterocycle by the joining of two groups and the nitrogen atom to which they are attached is to form a monocycle.

The term "$C_1$-$C_8$ alkyl" or "$C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkylaryl means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes phenyl, benzyl, naphthyl, but excludes carbazoles and other fused tricyclic ring structures.

It is understood by one of skill in the art that where a substituent is absent, a hydrogen atom is indicated to achieve the required valency unless otherwise indicated. For example, if y is o, then $R^4$ is absent, and all applicable positions on the ring have hydrogen atoms to achieve the required valency for atoms in the ring.

As used herein, the term "protecting group" refers to a groups useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, $3^{rd}$ edition, Greene, T. W.; Wuts, P. G. M. Eds.; John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, maleate, mandelate, mesylate, methylbromide, methylnitrate, methylsulfate, sulfite, sulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I may occur as any one of its positional isomers, stereochemical isomers or regio-isomers, or canonical forms or tautomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

The compounds of the present invention have shown inhibition of orexigenic effects, and are thus useful as appetite suppressants either as a single therapy or in conjunction with exercise and other effective appetite suppressing or weight loss medications.

PREFERRED EMBODIMENTS OF THE INVENTION

A compound of formula I preferably exists as the free base or a pharmaceutically acceptable salt. More preferred is the hydrochloride salt, the bisulfate salt, mesylate or the oxalic acid salt of the compound of formula I.

For the Groups $R^1$ and $R^2$

Preferred $R^1$ and $R^2$ groups are independently selected from the group consisting of hydrogen, methyl, ethyl, propyl, pentyl, and isopropyl. Also preferred are $R^1$ and $R^2$ groups independently selected from the group consisting of methyl, ethyl, propyl, isopropyl, phenyl,

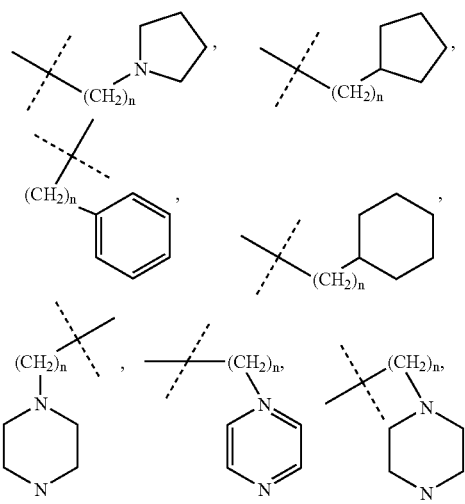

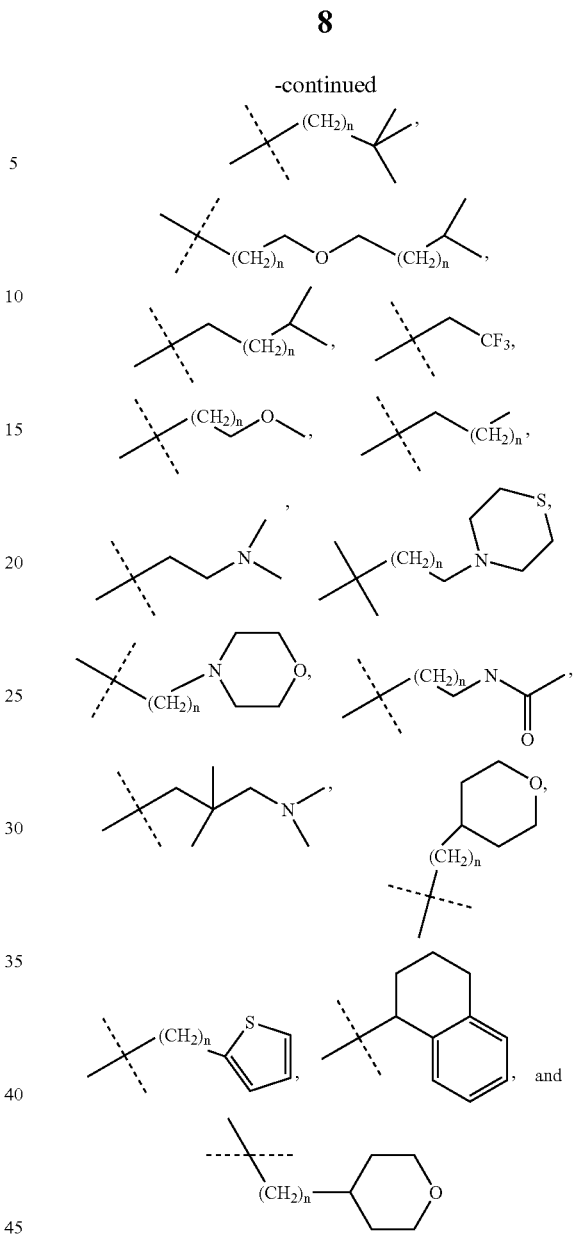

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle.

Also preferred are $R^1$ and $R^2$ groups which combine with each other to form a group selected from the group consisting of

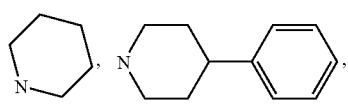

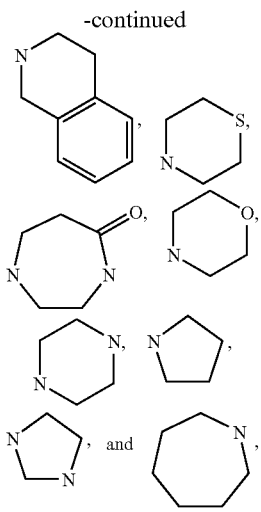

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, butyl, isobutyl, phenyl and benzyl. More preferably, both $R^3$ and $R^{3'}$ are hydrogen.

Preferred $R^4$ Groups

A preferred $R^4$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently absent, or singly substituted on their respective ring substrates.

Preferred $R^a$ and $R^b$ Groups

Preferably $R^a$ and $R^b$ are each hydrogen, or combine to form the vinylic diradical CH=CH when p is 2.

Preferred $R^5$ Groups

A preferred $R^5$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl C1-C5 alkylcycloalkyl, and $C_1$-$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopropyl, fluoro, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I wherein $R^6$ and $R^7$ independently combine with each other, and with the nitrogen atom to which they are attached to form a 4, 5, 6, or 7-membered nitrogen containing heterocycle which nitrogen containing heterocycle optionally has substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, C(O)$C_1$-$C_8$ alkyl, CO(O)$C_1$-$C_8$ alkyl, hydroxy, $C_1$-$C_8$ alkoxy, halo, and haloalkyl.

Most preferred are compounds of the invention wherein $R^6$ and $R^7$ are both hydrogen.

Preferred E Group

A most preferred E group is an oxygen atom (O).

Preferred A-Ring

A preferred A-ring is a phenyl ring or a pyridine ring.

Preferred B Ring

A preferred B ring is a 5, 6, or 7 membered ring. Also preferred is a B ring (ring B) wherein $(CR^aR^b)_p$ equals CH=CH.

Preferred C-Ring

A preferred C-ring is a phenyl ring, a pyrazine ring, a pyrimidine ring or a pyridine ring. Most preferred C ring is a phenyl ring or a pyridine ring.

Preferred Values for n, m, and p

A preferred value for n is 1 or 2.
A preferred value for m is 1 or 2.
A preferred value for p is 2.

A preferred compound according to the present invention is a compound selected from the group consisting of:

8-[(3-Methyl-butylamino)-methyl]-10,11-dihydro-dibenzo[b,f]oxepine-2-carboxylic acid amide, 8-(Isobutylamino-methyl)-10,11-dihydro-dibenzo[b,f]oxepine-2-carboxylic acid amide, 8-[(4-Methyl-pentylamino)-methyl]-10,11-dihydro-dibenzo[b,f]oxepine-2-carboxylic acid amide, 8-[(2-Thiophen-2-yl-ethylamino)-methyl]-10,11-dihydro-dibenzo[b,f]oxepine-2-carboxylic acid amide, 8-Pentylaminomethyl-10,11-dihydro-dibenzo[b,f]oxepine-2-carboxylic acid amide, 8-Hexylaminomethyl-10,11-dihydro-dibenzo[b,f]oxepine-2-carboxylic acid amide, 8-[(Cyclohexylmethyl-amino)-methyl]-10,11-dihydro-dibenzo[b,f]oxepine-2-carboxylic acid amide, 8-Cyclooctylaminomethyl-10,11-dihydro-dibenzo[b,f]oxepine-2-carboxylic acid amide, 8-Cycloheptylaminomethyl-10,11-dihydro-dibenzo[b,f]oxepine-2-carboxylic acid amide, 8-[(Cycloheptylmethyl-amino)-methyl]-10,11-dihydro-dibenzo[b,f]oxepine-2-carboxylic acid amide trifluoroacetate salt, 8-{[2-(Tetrahydro-pyran-4-yl)-ethylamino]-methyl}-10,11-dihydro-dibenzo[b,f]oxepine-2-carboxylic acid amide, 8-[(3,3-Dimethyl-butylamino)-methyl]-10,11-dihydro-dibenzo[b,f]oxepine-2-carboxylic acid amide, 8-[(2-Cyclopentyl-ethylamino)-methyl]-10,11-dihydro-dibenzo[b,f]oxepine-2-carboxylic acid amide, 8-[(3-Morpholin-4-yl-propylamino)-methyl]-10,11-dihydro-dibenzo[b,f]oxepine-2-carboxylic acid amide, 8-[(3-Ethoxy-propylamino)-methyl]-10,11-dihydro-dibenzo[b,f]oxepine-2-carboxylic acid amide, 8-[(2-Diethylamino-ethylamino)-methyl]-10,11-dihydro-dibenzo[b,f]oxepine-2-carboxylic acid amide,
8-[(3-Methoxy-propylamino)-methyl]-10,11-dihydro-dibenzo[b,f]oxepine-2-carboxylic acid amide, and
8-[(3-Phenyl-propylamino)-methyl]-10,11-dihydro-dibenzo[b,f]oxepine-2-carboxylic acid amide,
8-(3-Phenyl-pyrrolidin-1-ylmethyl)-10,11-dihydro-dibenzo[b,f]oxepine-2-carboxylic acid amide,
8-(3-Phenyl-piperidin-1-ylmethyl)-10,11-dihydro-dibenzo[b,f]oxepine-2-carboxylic acid amide,
8-[2-(4-Chloro-phenyl)-pyrrolidin-1-ylmethyl]-10,11-dihydro-dibenzo[b,f]oxepine-2-carboxylic acid amide,
8-(2-Phenyl-pyrrolidin-1-ylmethyl)-10,11-dihydro-dibenzo[b,f]oxepine-2-carboxylic acid amide,
8-(2-Phenyl-piperidin-1-ylmethyl)-10,11-dihydro-dibenzo[b,f]oxepine-2-carboxylic acid amide,
8-(2-Phenyl-azepan-1-ylmethyl)-10,11-dihydro-dibenzo[b,f]oxepine-2-carboxylic acid amide,
8-(2-Benzyl-pyrrolidin-1-ylmethyl)-10,11-dihydro-dibenzo[b,f]oxepine-2-carboxylic acid amide,
8-[(3-Methyl-butylamino)-methyl]-dibenzofuran-2-carboxylic acid amide,
8-[(3-Methyl-butylamino)-methyl]-10,11-dihydro-dibenzo[b,f]oxepine-2-carboxilic acid amide,
8-[(3-Methyl-butylamino)-methyl]-10,11-dihydro-5-oxa-4-aza-dibenzo[a,d]cycloheptene-2-carboxylic acid amide,
8-[(3-Methyl-butylamino)-methyl]-5-oxa-4-aza-dibenzo[a,d]cycloheptene-2-carboxylic acid amide, or a pharmaceutically acceptable salt, solvate, enantiomer, diastereomer and diastereomeric mixture thereof.

Preparing Compounds of the Invention

Compounds of formula I may be prepared as described in the following schemes and/or examples or following a combination of schemes know to one of skill in the art for making fragments and combinations thereof. Compounds employed as initial starting materials in the synthesis of compounds of the invention are well known and, to the extent not commercially available, are readily synthesized using specific references provided, or by standard procedures commonly employed by those of ordinary skill in the art and/or found in general reference texts.

More particularly, the compounds of the invention are produced in accordance with schemes 1 through 3 that are described in detail below, or analogous methods thereof. These reactions are often carried out following known procedures, methods, or analogous methods thereof. Examples of such known procedures and/or methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Compounds of the present invention are generally prepared starting with the corresponding dibenzo oxygenated tricycle 1 which is dibrominated to afford regioisomer 2, shown in scheme 1.

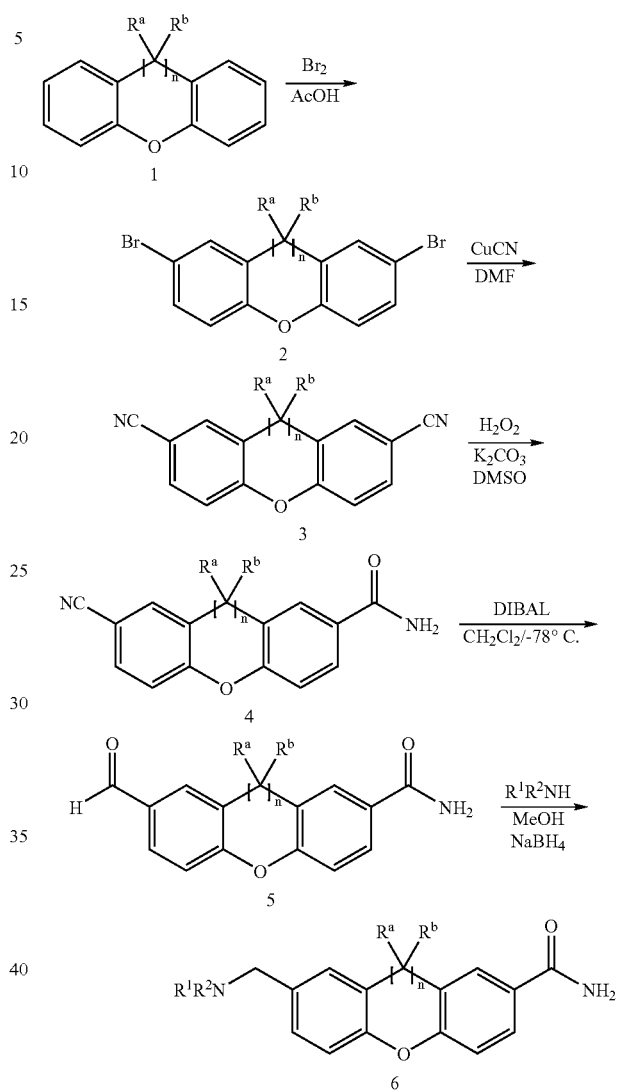

Scheme 1

Reaction with copper cyanide affords the dinitrile analog 3. De-symmetrization is achieved by mono-oxidation to the carboxamide 4. Preferably, a 50% but less than equivalent mole of reagents i.e. $H_2O_2/K_2CO_3$ is utilized to maximize de-symmetrization and minimize formation of the bis carboxamide compound. Further transformation of the remaining nitrile to an aldehyde with diisobutylaluminum hydride (DIBAL®) affords the compound 5. The compound 5 upon reductive amination affords the desired product 6. Details of specific procedures are provided in the scheme below and/or in the experimental section. The compound 6 may be converted to other compounds of the invention by elaborating the carboxamide functionality to N-substituted or N,N-disubstituted amide groups using procedures known to one of skill in the art and requiring minimal experimentation or research.

A preferred synthetic route for preparing compounds of formula I wherein Ring C is pyridine and the central ring (B) is a seven membered ring is shown in scheme 2.

Scheme 2

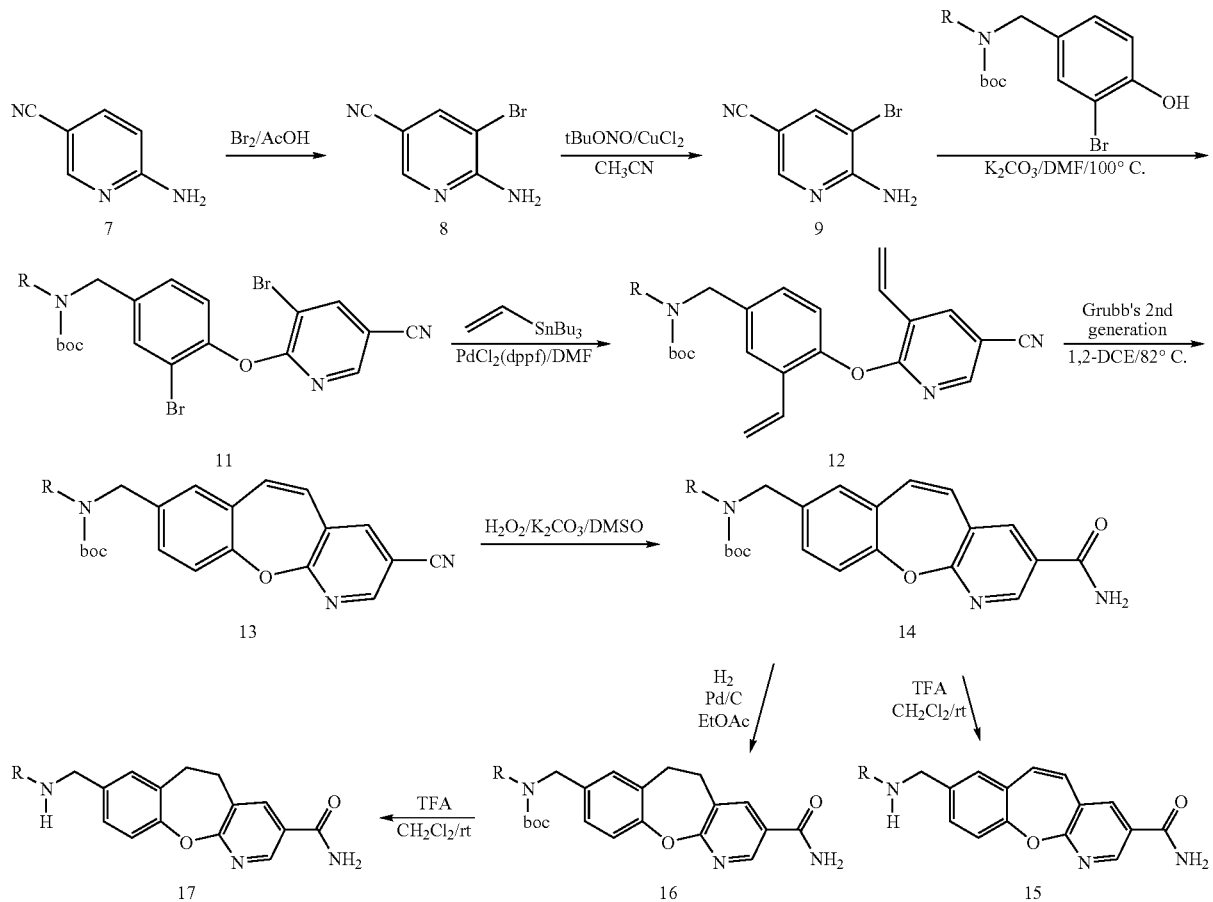

According to Scheme 2, 6-amino nicotinonitrile (7) is regioselectively brominated in the 5-position to afford the bromo compound 8. The free amine functionality of compound 8 is converted to the chloride as in compound 9. Compound 9 is coupled with the corresponding 3-bromo-4-hydroxybenzylic, N-tertbutyloxycarbonyl protected amine (10) to afford the coupled compound 11. Palladium catalyzed cross coupling of 11 with vinyl tributyl stannane affords the arylvinyl compound 12 (see Stille Coupling, *Angew Chemie, Int. Ed.* 25, 508, (1986) and related references). The divinyl derivative 12 undergoes an intramolecular methatesis affording the compound 13 (see Grubbs second generation *Tetrahedron* 54, 4413, (1998) and related references therein). The compound 13 is hydrolyzed under basic conditions to afford the carboxamide 14. For example, treatment of compound 13 with hydrogen peroxide in the presence of a base such as sodium carbonate in dimethylsulfoxide affords the carboxamide compound 14. The carboxamide 14 is then de-protected at the amine by reaction with, for example, trifluoroacetic acid in methylene chloride preferably at room temperature to afford 15, a compound of the invention. The carboxamide 14 is reduced under hydrogen atmosphere using palladium on carbon as catalyst to afford compound 16. Compound 16 is then de-protected at the amine by reaction with trifluoroacetic in methylene chloride to afford 17, a compound of the invention.

Alternatively, compound 17 is utilized to afford a disubstituted compound of the invention as shown in Scheme 3 below.

Scheme 3

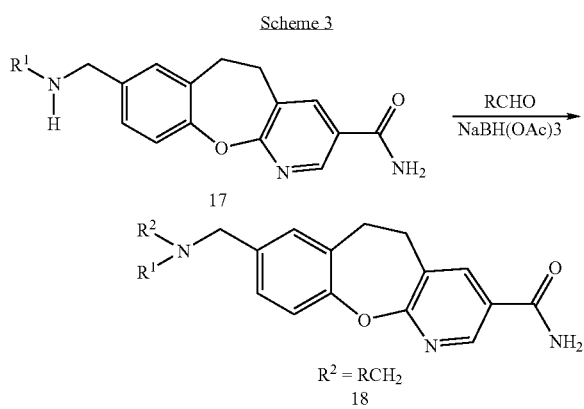

As shown in Scheme 3, compound 17 upon reductive amination affords the amine 18 (wherein neither $R^1$ nor $R^2$ is hydrogen).

Substituted analogs of compound 1 may be prepared following for example, a scheme such as Scheme 4

Scheme 4

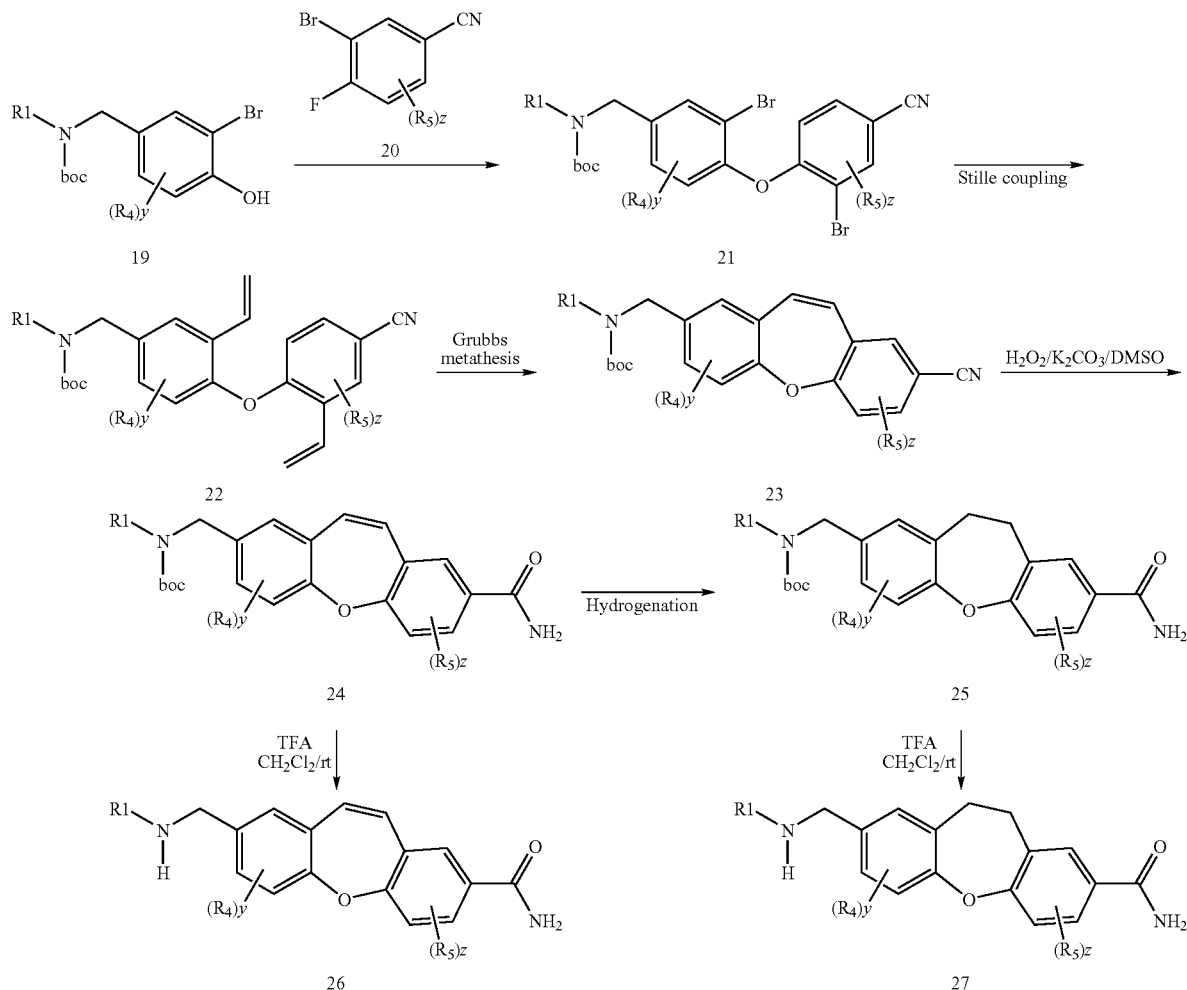

As shown in scheme 4, an optionally substituted Boc-protected amino 2-bromoaminophenol 19 may be coupled with an optionally substituted 3-bromo, 4-fluorobenzonitrile 20 to afford the coupled product 21. The coupling reaction is accomplished under basic reaction conditions as described previously. The coupled product 21 is reacted with vinyl tributyl stannane under Stille coupling conditions described previously to afford the vinylic compound 22. The compound 22 is then ring closed using the Grubbs methatesis procedure to afford the tricyclic compound 23. The cyano group of the compound 23 is hydrolyzed under basic conditions discussed previously to afford the carboxamide compound 24. The carboxamide compound 24 is reduced at the alkenyl group to afford the reduced compound 25, which is further deprotected at the boc group to afford the compound 27. Alternatively, the carboxamide 24 is deprotected at the amino group to afford the alekeny compound 26. One of skill in the art is aware that the use of a disubstituted amine compound as starting material in place of compound 19 would result following the protocol above in the disubstituted amine analog of compound 26 or 27.

An example of a compound of formula 20 is 3-bromo-3,4,5-trifluorobenzonitrile disclosed in European patent application EP 85/114373. Compounds of formula 19 may be prepared by methods known to one of skill in the art or may be available from commercial sources. For example, compounds of formula 19 may be prepared as shown in scheme 6.

Scheme 6

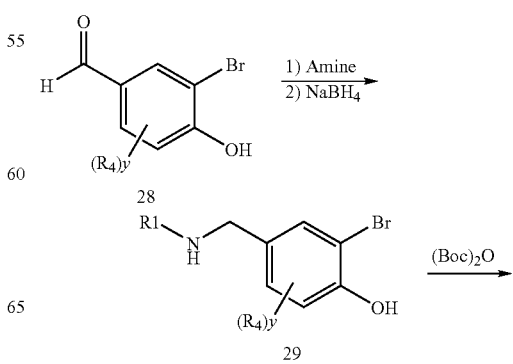

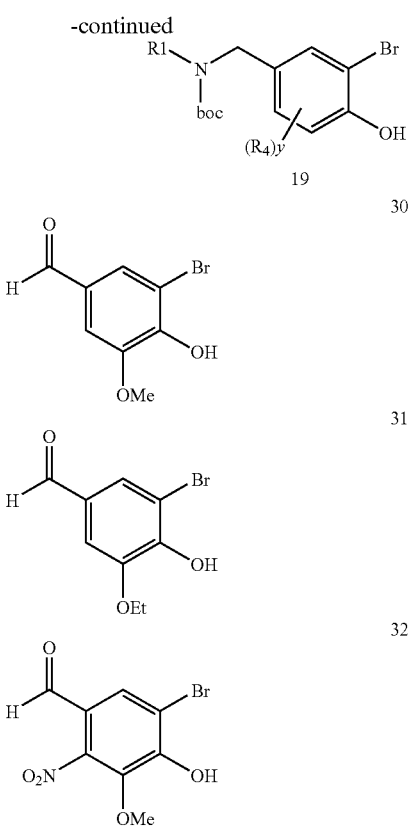

As shown in Scheme 6, a compound of formula 19 may be prepared starting with an optionally substituted hydroxybenzaldehyde 28, which is reductively aminated to the amine 29. The amine 29 is boc protected to afford the resulting amine 19. Specific examples of the optionally substituted compound 28 include compounds 30, 31, and 32 all of which are available from commercial sources.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof.

Assay Methodology

The compounds of the present invention have been found to display significant activity in an opioid receptor binding assay which measures the ability of the compounds to block the mu, kappa, delta or receptor combination (heterodimer) thereof. The functional antagonist potency (Kb) of the sample compounds was determined using the GTPγS binding assay. GTPgS—based functional assays provide an in vitro measure of the activity of opioid agonists and antagonists. Opioid reference compounds or test compound are incubated with membrane homogenate from cells expressing the cloned human mu, kappa or delta opioid receptor and radiolabeled [35S]GTPgS. If the compound activates the opioid receptor, an increase in the binding of radiolabeled GTPgS is observed. Similarly, if the compound exhibits antagonist activity, it interferes with the ability to control agonist to stimulate GTPgS binding. These tests provide an in vitro measurement of the activity of the compound at human opioid receptors.

GTP-γ-S Binding Assay

An SPA-based GTP-γ-S assay format was developed based on previous opioid (Emmerson et al., J. Pharm Exp Ther 278,1121,1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM MgCl$_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a sample of compounds of the invention the GTP-γ-S Binding Assay are shown in table 1 below.

TABLE 1

| Example # | Kb (nM) mu | Kb (nM) kappa | Kb (nM) delta |
|---|---|---|---|
| 1 | 1.2 | 6.1 | 11.0 |
| 2 | 12.0 | 29.8 | |
| 3 | 0.8 | 6.5 | 7.4 |
| 4 | 0.9 | 12.6 | 7.1 |
| 5 | 1.7 | 4.9 | |
| 6 | 0.7 | 4.4 | 10.3 |
| 12 | 0.7 | 2.2 | 2.1 |
| 13 | 4.0 | 12.1 | 14.4 |
| 14 | 0.6 | 8.6 | 7.0 |
| 17 | 2.1 | 25.7 | 26.7 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient therefore.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |

-continued

| Compound | Amount per capsule (mg) | Concentration by weight (%) |
|---|---|---|
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders, which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
|---|---|
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLES

Compounds of the invention may be prepared following procedures disclosed herein or known modifications thereof. Unless otherwise indicated, reagents are generally available from chemical distributors including those specializing in fine limited use chemicals.

Example 1

8-[(3-Methyl-butylamino)-methyl]-10,11-dihydro-dibenzo[b,f]oxepine-2-carboxilic acid amide Step 1

2,8-Dibromo-10,11-dihydro-dibenzo[b,f]oxepine

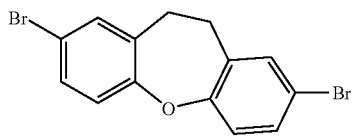

To a solution of (10,11-dihydro-dibenzo[b,f]oxepine* (2.7 g, 13.8 mmol) in AcOH (11 mL) add Br$_2$ 2.0 M (17.2 mL, 13.8 mmol) in AcOH. Stir the mixture at 55° C. for 4 hours. Cool the mixture at room temperature and eliminate the solvent under reduced pressure. Dissolve the crude in CH$_2$Cl$_2$ and wash with aqueous solution of NaHSO$_3$. Dry the organic layer over Na$_2$SO$_4$. Eliminate the solvent to obtain 4.9 g of the title compound (99%) which is used in the next step without purification.

$^1$H-NMR (CDCl$_3$, 300 MHz): 7.29-7.23 (m, 4H), 7.04-6.99 (m, 2H), 3.08 (s, 4H) $^{13}$C-NMR (CDCl$_3$, 500 MHz): 155.9, 133.8, 133.2, 130.6, 122.9, 116.8, 30.9.

*The synthesis of (10,11-dihydro-dibenzo[b,f]oxepine is described in *J. Am. Chem. Soc.* 1969, 91, 1665.

Step 2

10,11-dihydro-dibenzo[b,f]oxepine-2,8-dicarbonitrile

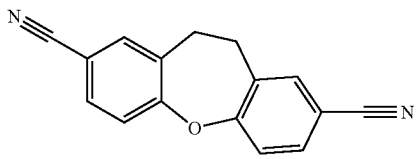

To a solution of the intermediate above (4.9 g, 13.8 mmol) in dry DMF (120 mL) add CuCN (8.6 g, 96.8 mmol), heat the mixture at 160° C. under $N_2$ atmosphere overnight. Cool the mixture at room temperature, add $NH_4OH$ and bubble air during 4 hours. Add cold (0-25° C.) water and extract with EtOAc, dry over $Na_2SO_4$. Eliminate the solvent under reduced pressure. Purify by flash chromatography on silica gel (eluent: hexane/EtOAc 4/1) to afford the title compound (2.0 g, 59%).

$^1$H-NMR (CDCl$_3$, 300 MHz): 7.54-7.48 (m, 4H), 7.28-7.22 (m, 2H), 3.17 (s, 4H). $^{13}$C-NMR (CDCl$_3$, 300 MHz): 158.0, 134.7, 132.5, 131.8, 122.2, 118.5, 107.5, 31.1.

Step 3

8-Cyano-10,11-dihydro-dibenzo[b,f]oxepine-2-carboxilic acid amide

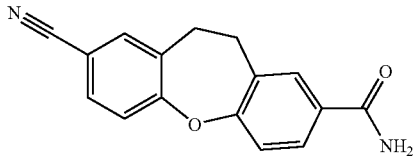

To a solution of the intermediate above (2.0 g, 8.1 mol) in dry DMSO (80 mL) add $K_2CO_3$ (562 mg, 4.06 mmol), cool the mixture at 0° C. and add $H_2O_2$ 33% (837 μl, 8.1 mmol) dropwise. Stir the mixture at room temperature overnight. Add cold (0-25° C.) water and extract with EtOAc, dry the organic layer over $Na_2SO_4$, and eliminate the solvent at reduced pressure. Purify the crude product by flash column chromatography on silica gel (eluent: EtOAc) to obtain the title compound (1.08 g, 48%).

$^1$H-NMR (MeOD, 300 MHz): 7.75-7.70 (m, 2H), 7.60-7.54 (m, 2H), 7.33-7.22 (m, 2H), 3.28 (m, 4H). $^{13}$C-NMR (MeOD, 300 MHz): 167.4, 159.4, 157.7, 135.6, 133.1, 132.2, 131.2, 130.7 (2C), 127.5, 122.5, 120.9, 118.9, 106.9, 30.8, 30.6.

Step 4

8-Formyl-10,11-dihydro-dibenzo[b,f]oxepine-2-carboxilic acid amide

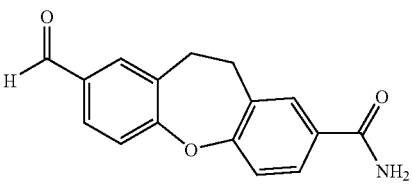

To a solution of the intermediate from step 3 (2.5 g, 9.5 mmol) in dry $CH_2Cl_2$ (320 mL), cooled at −78° C. and under $N_2$ atmosphere, add DIBAL 10M in toluene (28.4 mmol). Allow the mixture to warm to room temperature and stir overnight. Cool the mixture to 0° C. and add AcOH/$H_2O$. Stir at room temperature for 1 hour. Extract the aqueous layer with $CH_2Cl_2$ (×2). Combine the organic layers and dry over $Na_2SO_4$. Eliminate the solvent and purify by flash chromatography (eluent: EtOAc/hexane 3/1) to obtain the title compound (1.75 g, 69%). $^1$H-NMR (MeOD, 300 MHz): 9.91 (s, 1H), 7.81-7.73 (m, 4H), 7.37-7.26 (m, 2H), 3.21 (m, 4). $^{13}$C-NMR (MeOD, 300 MHz): 193.2, 162.6, 160.3, 134.4, 133.8, 133.2, 131.9, 131.3, 130.6, 128.8, 123.3, 122.4, 32.9, 32.8.

Step 5

8-[(3-Methyl-butylamino)-methyl]-10,11-dihydro-dibenzo[b,f]oxepine-2-carboxilic acid amide

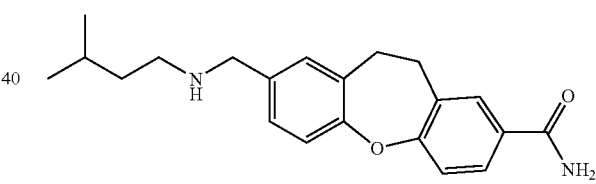

Combine intermediate step 4 (250 mg, 0.94 mmol) with 3-methylbutylamine (110 μL, 0.94 mmol), MeOH (12 mL) and molecular sieves 3A (1.5 g). Stir at room temperature overnight. Add NaBH4 (178 mg, 4.7 mmol) and stir at room temperature for 2 hours. Filtrate over celite with MeOH and eliminate the solvent. Purify using SCX ion-exchange chromatography to afford the title compound (300 mg, 91%).

By the method of example 1, using the corresponding reagents, the following compounds (examples 2-20) were prepared. The purification process depends on the structure of the corresponding example.

| Example | Name | Electrospray MS M+1 ion | $^1$H-NMR (300 MHz, CD$_3$OD) |
|---|---|---|---|
| 1 | 8-[(3-Methyl-butylamino)-methyl]-10,11-dihydro- | 339 | 7.70-7.66(m, 2H), 7.20-7.08(m, 4H), 3.70(s, 2H), 3.14(m, 4H), 2.63-2.55(m, 2H), 1.63-1.36(m, |

-continued

| Example | Name | Electrospray MS M+1 ion | $^1$H-NMR (300 MHz, CD$_3$OD) |
|---|---|---|---|
| | dibenzo[b,f]oxepine-2-carboxylic acid amide | | 3H), 0.89(d, 6H, J=6.9 Hz) |
| 2 | 8-(Isobutylamino-methyl)-10,11-dihydro-dibenzo[b,f]oxepine-2-carboxylic acid amide | 325 | 7.73-7.69(m, 2H), 7.22-7.12(m, 4H), 3.75(s, 2H), 3.17(bs, 4H), 2.44(d, 2H, J=6.8 Hz), 1.91-1.78(m, 1H), 0.93(d, 6H, J=6.7 Hz). |
| 3 | 8-[(4-Methyl-pentylamino)-methyl]-10,11-dihydro-dibenzo[b,f]oxepine-2-carboxylic acid amide | 353 | 7.75-7.70(m, 2H), 7.26-7.18(m, 4H), 3.91(s, 2H), 3.19(bs, 4H), 2.79-2.74(m, 2H), 1.67-1.53(m, 2H), 1.31-1.20(m, 3H), 0.92(d, 6H, J=6.7 Hz) |
| 4 | 8-[(2-Thiophen-2-yl-ethylamino)-methyl]-10,11-dihydro-dibenzo[b,f]oxepine-2-carboxylic acid amide | 379 | 7.64-7.59(m, 2H), 7.12-7.04(m, 5H), 6.85-6.82(m, 1H), 6.76(m, 1H), 3.64(s, 2H), 3.10-3.03(m, 4H), 2.95(t, 2H, J=7.6 Hz), 2.77(t, 2H, J=7.3 Hz) |
| 5 | 8-Pentylaminomethyl-10,11-dihydro-dibenzo[b,f]oxepine-2-carboxylic acid amide | 339 | 7.64-7.59(m, 2H), 7.12-7.02(m, 4H), 3.61(s, 2H), 3.07(bs, 4H), 2.50-2.45(m, 2H), 1.49-1.40(m, 2H), 1.30-1.15(m, 4H), 0.83(t, 3H, J=6.9 Hz) |
| 6 | 8-Hexylaminomethyl-10,11-dihydro-dibenzo[b,f]oxepine-2-carboxylic acid amide | 353 | 7.64-7.59(m, 2H), 7.12-7.02(m, 4H), 3.62(s, 2H), 3.07(bs, 4H), 2.51-2.46(m, 2H), 1.47-1.39(m, 2H), 1.28-1.14(m, 6H), 0.80(t, 3H, J=6.9 Hz) |
| 7 | 8-[(Cyclohexylmethyl-amino)-methyl]-10,11-dihydro-dibenzo[b,f]oxepine-2-carboxylic acid amide | 365 | 7.63-7.59(m, 2H), 7.12-7.01(m, 4H), 3.59(s, 2H), 3.07(bs, 4H), 2.30(d, 2H, J=6.8 Hz), 1.69-1.57(m, 5H), 1.46-1.35(m, 1H), 1.27-1.09(m, 3H), 0.87-0.75(m, 2H) |
| 8 | 8-Cyclooctylaminomethyl-10,11-dihydro-dibenzo[b,f]oxepine-2-carboxylic acid amide | 379 | 7.63-7.59(m, 2H), 7.12-7.01(m, 4H), 3.60(s, 2H), 3.07(bs, 4H), 2.64-2.58(m, 1H), 1.76-1.31(m, 14H). |
| 9 | 8-Cycloheptylaminomethyl-10,11-dihydro-dibenzo[b,f]oxepine-2-carboxylic acid amide | 365 | 7.63-7.59(m, 2H), 7.12-7.01(m, 4H), 3.60(s, 2H), 3.07(bs, 4H), 2.60-2.51(m, 1H), 1.86-1.78(m, 2H), 1.65-1.31(m, 10H) |
| 10 | 8-[(Cycloheptylmethyl-amino)-methyl]-10,11-dihydro-dibenzo[b,f]oxepine-2-carboxylic acid amide trifluoroacetate salt | 379 | 7.64-7.59(m, 2H), 7.12-7.01(m, 4H), 3.59(s, 2H), 3.07(bs, 4H), 2.30(d, 2H, J=6.5 Hz), 1.68-1.04(m, 13H) |
| 12 | 8-{[2-(Tetrahydro-pyran-4-yl)-ethylamino]-methyl}-10,11-dihydro-dibenzo[b,f]oxepine-2-carboxylic acid amide | 381 | 7.75-7.71(m, 2H), 7.24-7.13(m, 4H), 3.41(dd, 2H, J=4.0 and 11.3 Hz), 3.73/s, 2H), 3.40(dt, 2H, J=1.6 and 11.7 Hz), 3.18(bs, 4H), 2.66-2.61(m, 2H), 1.63-1.46(m, 5H), 1.34-1.25(m, 2H) |
| 13 | 8-[(3,3-Dimethyl-butylamino)-methyl]-10,11-dihydro-dibenzo[b,f]oxepine-2-carboxylic acid amide | 353 | 7.64-7.59(m, 2H), 7.12-7.02(m, 4H), 3.61(s, 2H), 3.06(bs, 4H), 2.54-2.49(m, 2H), 1.39-1.34(m, 2H), 0.92(s, 9H) |
| 14 | 8-[(2-Cyclopentyl-ethylamino)-methyl]-10,11-dihydro-dibenzo[b,f]oxepine-2-carboxylic acid amide | 365 | 7.64-7.59(m, 2H), 7.13-7.02(m, 4H), 3.62(s, 2H), 3.07(bs, 4H), 2.53-2.48(m, 2H), 1.76-1.44(m, 9H), 1.07-1.00(m, 2H) |
| 15 | 8-[(2-Morpholin-4-yl-ethylamino)-methyl]-10,11-dihydro-dibenzo[b,f]oxepine-2-carboxylic acid amide | 382 | 7.64-7.59(m, 2H), 7.13-7.02(m, 4H), 3.63(s, 2H), 3.59-3.55(m, 4H), 3.07(bs, 4H), 2.60(t, 2H, J=6.9 Hz), 2.41(t, 2H, J=6.6 Hz), 2.34-2.31(m, 4H) |
| 16 | 8-[(3-Morpholin-4-yl-propylamino)-methyl]-10,11-dihydro-dibenzo[b,f]oxepine-2-carboxylic acid amide | 396 | 7.64-7.59(m, 2H), 7.12-7.02(m, 4H), 3.61(s, 2H), 3.59-3.55(m, 4H), 3.07(bs, 4H), 2.54(t, 2H, J=7.2 Hz), 2.37-2.27(m, 6H), 1.68-1.58(m, 2H) |

| Example | Name | Electronspray MS M+1 ion | $^1$H-NMR (300 MHz, CD$_3$OD) |
|---|---|---|---|
| 17 | 8-[(3-Ethoxy-propylamino)-methyl]-10,11-dihydro-dibenzo[b,f]oxepine-2-carboxylic acid amide | 355 | 7.62-7.58(m, 2H), 7.10-6.99(m, 4H), 3.59(s, 2H), 3.39-3.32(m, 4H), 3.02(bs, 4H), 2.57(t, 2H, J=6.9 Hz), 1.72-1.63(m, 2H), 1.05(t, 3H, J=7.2 Hz) |
| 18 | 8-[(2-Diethylamino-ethylamino)-methyl]-10,11-dihydro-dibenzo[b,f]oxepine-2-carboxylic acid amide | 368 | 7.64-7.59(m, 2H), 7.13-7.03(m, 4H), 3.64(s, 2H), 3.07(bs, 4H), 2.62-2.43(m, 8H), 0.94(t, 6H, J=7.2 Hz) |
| 19 | 8-[(3-Methoxy-propylamino)-methyl]-10,11-dihydro-dibenzo[b,f]oxepine-2-carboxylic acid amide | 341 | 7.73-7.69(m, 2H), 7.22-7.11(m, 4H), 3.71(s, 2H), 3.49(t, 2H, J=6.9 Hz), 3.33(s, 3H), 3.19(bs, 4H), 2.66(t, 2H, J=7.1 Hz), 1.83-1.74(m, 2H) |
| 20 | 8-[(3-Phenyl-propylamino)-methyl]-10,11-dihydro-dibenzo[b,f]oxepine-2-carboxylic acid amide | 387 | 7.72-7.69(m, 2H), 7.24-7.05(m, 9H), 3.65(s, 2H), 3.11(bs, 4H), 2.63-2.54(m, 4H), 1.87-1.77(m, 2H) |

Example 21

8-{[Cyclopropylmethyl-(3-methyl-butyl)-amino]-methyl}-10,11-dihydro-dibenzo[b,f]oxepine-2-carboxylic acid amide

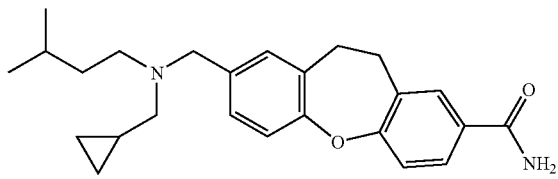

To a solution of amine of example 1 (30 mg, 0.09 mmol) in MeOH-AcOH 5% (0.5 mL) add cyclopropanecarboxaldehyde (0.18 mmol). Stir the mixture at room temperature overnight. Add NaBH$_3$CN and stir the mixture at room temperature for about two hours. Add more aldehyde (1.5 mmol) and stir overnight. Purify by SCX ion-exchange chromatography to obtain the title compound (22 mg). $^1$H-NMR (CD$_3$OD, 300 MHz): 7.72-7.69 (m, 2H), 7.21-7.09 (m, 4H), 3.64 (s, 2H), 3.14 (bs, 4H), 2.61-2.56 (m, 2H), 2.37 (d, 2H, J=6.5 Hz), 1.60-1.37 (m, 4H), 0.87 (d, 6H, J=6.7 Hz), 0.55-0.49 (m, 2H), 0.13-0.08 (m, 2H). Electrospray MS M+1 ion=393.

By the method of example 21, using the corresponding reagents, the following compounds (examples 22-23) were prepared. The purification process depends on the structure of the corresponding example.

Example 22

8-{[Cyclohexylmethyl-(3-methyl-butyl)-amino]-methyl}-10,11-dihydro-dibenzo[b,f]oxepine-2-carboxylic acid amide

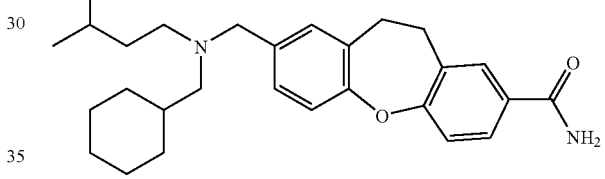

$^1$H-NMR (CD$_3$OD, 300 MHz): 7.72-7.69 (m, 2H), 7.21-7.07 (m, 4H), 3.44 (s, 2H), 3.16-3.12 (m, 4H), 2.61-2.56 (m, 2H), 2.36 (t, 2H, J=7.1 Hz), 2.16 (d, 2H, J=7.1 Hz), 1.84-1.13 (m, 12H), 0.83 (d, 6H, J=6.8 Hz). Electrospray MS M+1 ion=435.

Example 23

8-{[Methyl-(3-methyl-butyl)-amino]-methyl}-10,11-dihydro-dibenzo[b,f]oxepine-2-carboxylic acid amide trifluoroacetate salt

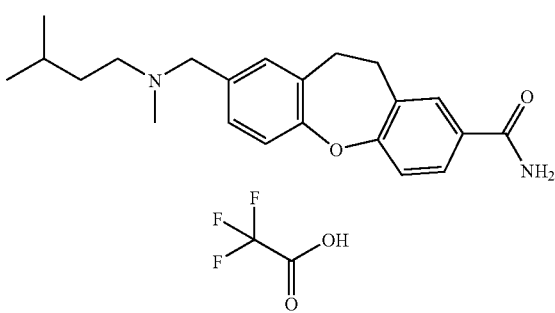

$^1$H-NMR (CD$_3$OD, 300 MHz): 7.76-7.72 (m, 2H), 7.37-7.23 (m, 4H), 4.43-4.16 (m, 2H), 3.21-3.10 (m, 6H), 2.79 (s, 3H), 1.67 (m, 3H), 0.98 (d, 6H; J=6.7 Hz). Electrospray MS M+1 ion=353.

Example 24

8-(3-Phenyl-pyrrolidin-1-ylmethyl)-10,11-dihydro-dibenzo[b,f]oxepine-2-carboxylic acid amide

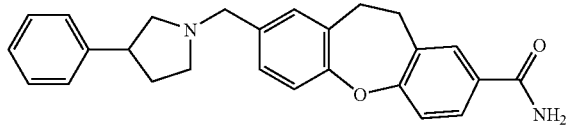

To a solution of aldehyde intermediate obtained in step 4, Example 1 (92 mg, 0.34 mmol) in THF/AcOH (6.5 mL/30 µL) add 3-phenylpyrrolidine (0.34 mmol). Stir the mixture at room temperature overnight. Add NaBH(OAc)$_3$ (0.52 mmol) and stir at room temperature overnight. Eliminate the solvent and purify by ISCO chromatography (eluent: CHCl$_3$/B 0-10%; B: EtOH/NH$_4$OH 10%).

By the method of example 24, using the corresponding reagents, the following compounds (examples 25-30) were prepared. The purification process depends on the structure of the corresponding example.

| Example | Name | Electrospray MS M+1 ion | $^1$H-NMR (300 MHz, CDCl$_3$) |
|---|---|---|---|
| 24 | 8-(3-Phenyl-pyrrolidin-1-ylmethyl)-10,11-dihydro-dibenzo[b,f]oxepine-2-carboxylic acid amide | 399 | 7.65(d, 1H, J=2.4 Hz), 7.57(dd, 1H, J=2.4 and 8.5 Hz), 7.33-7.09(m, 9H), 3.67(s, 2H), 3.49-3.35(m, 1H), 3.21-3.07(m, 5H), 2.93-2.90(m, 1H), 2.76-2.72(m, 1H), 2.56-2.50(m, 1H), 2.42-2.29(m, 1H), 2.02-1.88(m, 1H) |
| 25 | 8-(3-Phenyl-piperidin-1-ylmethyl)-10,11-dihydro-dibenzo[b,f]oxepine-2-carboxylic acid amide | 413 | 7.65(d, 1H, J=2.4 Hz), 7.56(dd, 1H, J=2.4 and 8.5 Hz), 7.30-7.08(m, 9H), 3.49(s, 2H), 3.19-3.11(m, 4H), 3.00-2.83(m, 3H), 2.07-1.90(m, 3H), 1.76(bs, 2H), 1.52-1.38(m, 1H) |
| 26 | 8-[2-(4-Chloro-phenyl)-pyrrolidin-1-ylmethyl]-10,11-dihydro-dibenzo[b,f]oxepine-2-carboxylic acid amide | 433 | 7.74-7.70(m, 2H), 7.43(d, 2H, J=8.5 Hz), 7.33(d, 2H, J=8.6 Hz), 7.20(d, 1H, J=8.3 Hz), 7.08(bs, 3H), 3.68(d, 1H, J=12.9 Hz), 3.40-3.33(m, 1H), 3.18-3.05(m, 6H), 2.31-2.19(m, 2H), 1.92-1.62(m, 3H) |
| 27 | 8-(2-Phenyl-pyrrolidin-1-ylmethyl)-10,11-dihydro-dibenzo[b,f]oxepine-2-carboxylic acid amide | 399 | 7.65(d, 1H, J=2.0 Hz), 7.56(dd, 1H, J=2.4 and 8.5 Hz), 7.46-7.43(m, 2H), 7.36-7.31(m, 2H), 7.27-7.17(m, 2H), 7.07-7.03(m, 3H), 3.76(d, 1H, J=12.9 Hz), 3.33(t, 1H, J=8.5 Hz), 3.16-3.05(m, 4H), 2.98(d, 1H, J=12.9 Hz), 2.24-2.12(m, 2H), 1.95-1.66(m, 4H) |
| 28 | 8-(2-Phenyl-piperidin-1-ylmethyl)-10,11-dihydro-dibenzo[b,f]oxepine-2-carboxylic acid amide | 413 | 7.56(d, 1H, J=2.0 Hz), 7.47(dd, 1H, J=2.4 and 8.1 Hz), 7.36-7.33(m, 2H), 7.23(t, 2H, J=6.9 Hz), 7.16-7.08(m, 2H), 6.97-6.90(m, 3H), 3.59(d, 1H, J=13.3 Hz), 3.08-2.96(m, 5H), 2.88-2.84(m, 1H), 2.66(d, 1H, J=13.3 Hz), 1.82(td, 1H, J=2.7 and 11.3 Hz), 1.70-0.74(m, 6H) |

| Example | Name | Electrospray MS M+1 ion | $^1$H-NMR (300 MHz, CDCl$_3$) |
|---|---|---|---|
| 29 | 8-(2-Phenyl-azepan-1-ylmethyl)-10,11-dihydro-dibenzo[b,f]oxepine-2-carboxylic acid amide | 427 | 7.56(d, 1H, J=2.0 Hz), 7.47(dd, 1H, J=2.0 and 8.1 Hz), 7.39-7.36(m, 2H), 7.22(t, 2H, J=6.9 Hz), 7.13-7.08(m, 2H), 7.04-6.93(m, 3H), 3.60(t, 1H, J=6.1 Hz), 3.49(d, 1H, J=14.1 Hz), 3.23(d, 1H, J=13.7 Hz), 3.08-2.98(m, 4H), 2.79(dd, 1H, J=6.9 and 14.5 Hz), 2.59(dd, 1H, J=1H, J=6.9 and 14.1 Hz), 1.86-1.40(m, 8H) |
| 30 | 8-(2-Benzyl-pyrrolidin-1-ylmethyl)-10,11-dihydro-dibenzo[b,f]oxepine-2-carboxylic acid amide | 413 | 7.57(d, 1H, J=2.4 Hz), 7.48(dd, 1H, J=2.4 and 8.5 Hz), 7.21-7.00(m, 9H), 3.95(d, 1H, J=12.9 Hz), 3.15-2.94(m, 5H), 2.84(dt, 1H, J=2.4 and 8.3 Hz), 2.60-2.41(m, 2H), 2.06(q, 1H, J=8.1 Hz), 1.71-1.44(m, 5H) |

Example 31

8-[(3-Methyl-butylamino)-methyl-10,11-dihydro-dibenzo[b,f]oxepine-2-carboxilic acid amide hydrochloride salt example 1

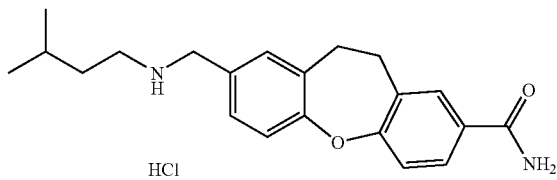

Dissolve amine of example I in 1N hydrochloric acid in AcOEt. Isolate the white precipitate by vacuum filtration to obtain the title compound. $^1$H-NMR (CD$_3$OD, 300 MHz): 7.91-7.86 (m, 2H), 7.50-7.37 (m, 4H), 4.31 (s, 2H), 3.36 (s, 4H), 3.24-3.18 (m, 2H), 1.89-1.70 (m, 3H), 1.13 (d, 6H, J=6.5 Hz). Electrospray MS M+1 ion=339.

Example 32

8-[(3-Methyl-butylamino)-methyl]-10,11-dihydro-dibenzo[b,f]oxepine-2-carboxilic acid amide methanesulfonate salt

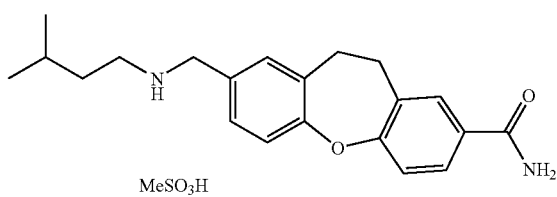

Dissolve amine of example 1 in THF (0.1M solution). Add metanesulfonic acid (1 equiv). Isolate the white precipitate by vacuum filtration to obtain the title compound. $^1$H-NMR (CD$_3$OD, 300 MHz): 7.90-7.87 (m, 2H), 7.51-7.37 (m, 4H), 4.31 (s, 2H), 3.36 (s, 4H), 3.22-3.19 (m, 2H), 2.87 (s, 3H), 1.86-1.73 (m, 3H), 1.14 (d, 6H, J=6.5 Hz). Electrospray MS M+1 ion=339.

Example 33

8-[(2-Morpholin-4-yl-ethylamino)-methyl]-10,11-dihydro-dibenzo[b,f]oxepine-2-carboxylic acid amide dimethanesulfonate salt

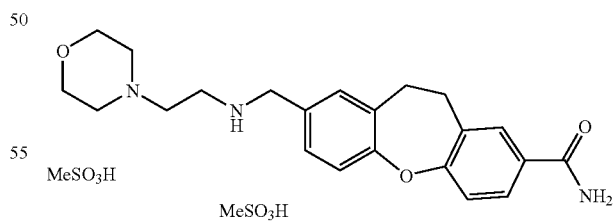

Dissolve amine of example 15 in THF (0.1M solution). Add metanesulfonic acid (1 equiv). Isolate the white precipitate by vacuum filtration. $^1$H-NMR (CD$_3$OD, 300 MHz): 7.73-7.69 (m, 2H), 7.42-7.38 (m, 2H), 7.27-7.20 (m, 2H), 4.27 (s, 2H), 4.04 (bs, 2H), 3.88 (bs, 2H), 3.58 (m, 6H), 3.18 (m, 6H), 2.70 (s, 6H). Electrospray MS M+1 ion=382.

Example 34

8-[(3-Morpholin-4-yl-propylamino)-methyl]-10,11-dihydro-dibenzo[b,f]oxepine-2-carboxylic acid amide dimethanesulfonate salt

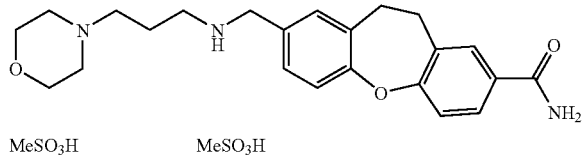

Dissolve amine of example 16 in THF (0.1M solution). Add metanesulfonic acid (1 equiv). Isolate the white precipitate by vacuum filtration. $^1$H-NMR (CD$_3$OD, 300 MHz): 7.73-7.69 (m, 2H), 7.38-7.35 (m, 2H), 7.27-7.20 (m, 2H), 4.20 (s, 2H), 3.86 (bs, 4H), 3.19-3.13 (m, 12H), 2.71 (s, 6H), 2.22-2.06 (m, 2H). Electrospray MS M+1 ion=396.

Example 35

8-[(3-Methyl-butylamino)-methyl]-dibenzofuran-2-carboxylic acid amide

Step 1

Dibenzofuran-2,8-dicarbonitrile

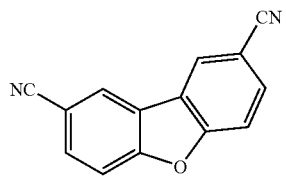

To a solution of 2,8-Diiodo-dibenzofuran (763 mg, 1.8 mmol) in dry DMF (16 mL) add CuCN (1.1 g, 12.7 mmol), heat the mixture at 160° C. under N$_2$ atmosphere overnight. Cool the mixture at room temperature, add NH$_4$OH and bubble air during 4 hours. Add cool water and extract with EtOAc, dry over Na$_2$SO$_4$. Eliminate the solvent under reduced pressure. Purify by flash chromatography on silica gel (eluent: hexane/EtOAc 3/1) to afford the title compound (25 mg, 6%).

$^1$H-NMR (DMSO, 200 MHz): 8.81 (dd, 2H, J=0.8 and 1.6 Hz), 8.11-8.06 (m, 2H), 8.03-7.99 (m, 2H).

Step 2

8-Cyano-dibenzofuran-2-carboxylic acid amide

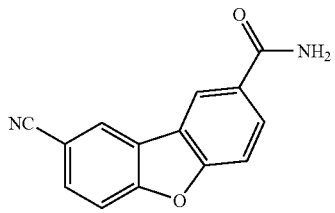

To a solution of the intermediate above (22 mg, 0.1 mmol) in dry DMSO (1 mL) add K$_2$CO$_3$ (7 mg, 0.05 mmol), cool the mixture at 0° C. and add H$_2$O$_2$ 33% (11 μl, 0.1 mmol) dropwise. Stir the mixture at room temperature overnight. Add cool water and extract with EtOAc, dry the organic layer over Na$_2$SO$_4$, eliminate the solvent at reduced pressure. Purify by flash chromatography on silica gel (eluent: EtOAc) to obtain the title compound (15 mg, 62%).

$^1$H-NMR (DMSO, 300 MHz): 8.79 (d, 2H, J=1.2 Hz), 8.13 (dd, 1H, J=1.8 and 8.7 Hz), 8.11 (bs, 1H), 8.03 (dd, 1H; J=1.4 and 8.5 Hz), 7.98 (d, 1H, J=8.3 Hz), 7.86 (d, 1H, J=8.9 Hz), 7.49 (bs, 1H).

Step 3

8-Formyl-dibenzofuran-2-carboxylic acid amide

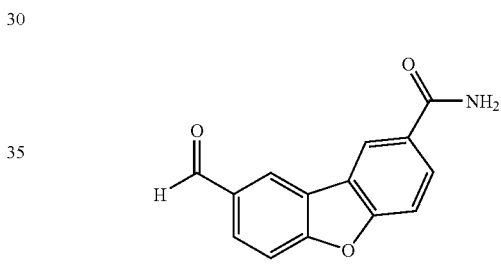

To a suspension of the intermediate above (15 mg, 0.07 mmol) in dry CH$_2$Cl$_2$ (3 mL), cooled at −78° C. and under N$_2$ atmosphere, add DIBAL 1.0M in toluene (0.25 mmol). Stir the mixture for 1 hour. Add AcOH/H$_2$O. Stir at room temperature for 1 hour. Extract the aqueous layer with EtOAc (×2), combined organic layers and dry over Na$_2$SO$_4$. Eliminate the solvent and purify by flash chromatography (eluent: EtOAc/hexane 4/1) to obtain the title compound (10 mg, 61%). $^1$H-NMR (MeOD, 300 MHz): 10.15 (s, 1H), 8.73 (m, 2H), 8.18-8.13 (m, 2H), 7.84 (d, 1H, J=8.7 Hz), 7.76 (dd, 1H, J=0.6 and 8.7 Hz).

Step 4

8-[(3-Methyl-butylamino)-methyl]-10,11-dihydro-dibenzo[b,f]oxepine-2-carboxilic acid amide

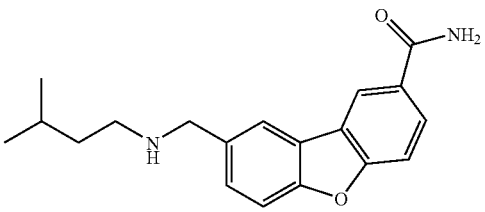

Combine intermediate above (10 mg, 0.04 mmol) with 3-methylbutylamine (5 μL, 0.04 mmol), MeOH (1 mL) and molecular sieves 3A (60 mg) and stir at room temperature overnight. Add NaBH$_4$ (8 mg, 0.2 mmol) and stir at room temperature for 2 hours. Filtrate over celite with MeOH and eliminate the solvent. Purify using SCX ion-exchange chromatography. The solid obtained was submitted to HPLC purification (the purification was carried out using basic conditions with 60% of Am. Bicarbonate at pH 8 and 40% of acetonitrile) to afford the title compound (5.5 mg, 43%).

$^1$H-NMR (CD$_3$OD, 300 MHz): 8.62 (s, 1H), 8.11-8.05 (m, 2H), 7.68-7.55 (m, 3H), 4.02 (s, 2H), 2.78-2.73 (m, 2H), 1.72-1.59 (m, 1H), 1.51 (q, 2H, J=7.0 Hz), 0.94 (d, 6H, J=6.6 Hz). Electrospray MS M+1 ion=311.

Example 36

8-[(3-Methyl-butylamino)-methyl]-10,11-dihydro-5-oxa-4-aza-dibenzo[a,d]cycloheptene-2-carboxylic acid amide Step 1

6-Amino-5-bromo-nicotinonitrile

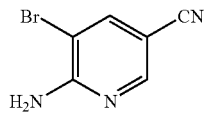

To a solution of 6-Amino-nicotinonitrile (102 mg, 0.86 mmol) in AcOH (2 mL) add a solution of Br$_2$ 1.0M in AcOH (0.86 mmol). Stir the mixture at room temperature for 2 hours. Eliminate the solvent. Purify by flash chromatography on silica gel (eluent: hexane/EtOAc 3/1) to afford the title compound (110 mg, 65%).

$^1$H-NMR (DMSO, 300 MHz): 8.26 (d, 1H, J=2.0 Hz), 8.10 (d, 1H, J=2.0 Hz), 7.24 (bs, 2H). MS (APCI Neg): 196, 198

Step 2

5-Bromo-6-chloro-nicotinonitrile

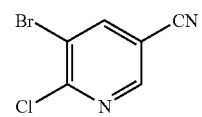

To a solution of anhydrous CuCl$_2$ (77 mg, 0.58 mmol) in CH$_3$CN (3 mL) add tert-BuONO (0.72 mmol). Heat the mixture at 65° C. and then add a suspension of the intermediate above (96 mg, 0.48 mmol) in CH$_3$CN (2 mL). Stir the mixture for 3 hours. Cool at room temperature. Pour into HCl 3M and extract with EtOAc. Dry the organic layer over Na$_2$SO$_4$. Eliminate the solvent. Purify by flash chromatography on silica gel (eluent: hexane/EtOAc 2/1) to afford the title compound (55 mg, 55%).

$^1$H-NMR (DMSO, 300 MHz): 8.93 (s, 1H), 8.90 (s, 1H).

Step 3

2-Bromo-4-[(3-methyl-butylamino)-methyl]-phenol

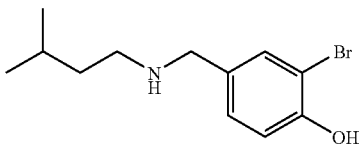

Combine 3-Bromo-4-hydroxy-benzaldehyde (1.5 g, 7.5 mmol) with 3-methylbutylamine (867 μL, 7.5 mmol), MeOH (25 mL) and molecular sieves 3A (5.8 g) and stir at room temperature overnight. Add NaBH$_4$ (1.4 g, 37.3 mmol) and stir at room temperature for 2 hours. Filtrate over celite with MeOH and eliminate the solvent. Purify by SCX ion-exchange chromatography to afford the title compound (1.5 g, 75%). $^1$H-NMR (CD$_3$OD, 300 MHz): 7.52 (d, 1H, J=2.0 Hz), 7.17 (dd, 1H, J=2.0 and 8.5 Hz), 6.87 (d, 1H, J=8.5 Hz), 3.80 (s, 2H), 2.79-2.74 (m, 2H), 1.76-1.63 (m, 1H), 1.54 (q, 2H, J=6.8 Hz), 0.99 (d, 6H, J=6.56 Hz). $^{13}$C-NMR (CD$_3$OD, 300 MHz): 158.6, 134.9, 130.7, 128.6, 118.8, 112.7, 53.3, 47.9, 38.6, 27.8, 23.3.

Step 4

(3-Bromo-4-hydroxy-benzyl)-(3-methyl-butyl)-carbamic acid tert-butyl ester

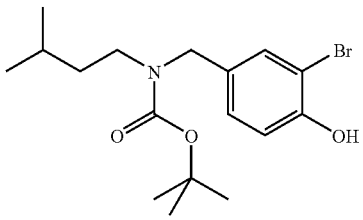

Dissolve intermediate above (800 mg, 2.94 mmol) in dry THF (5 mL) under N$_2$.atmosphere. Add a solution of di-tert-butyl dicarbonate (642 mg, 2.94 mmol) in dry THF (4 mL). Stir the mixture at room temperature overnight. Eliminate the solvent. Purify by ISCO chromatography (eluent: EtOAc/hexane 1/5) to obtain the title compound (850 mg, 78%). $^1$H-NMR (CDCl$_3$, 300 MHz): 7.34 (s, 1H), 7.07 (bs, 1H), 6.96 (d, 1H; J=8.1 Hz), 4.13 (bs, 2H), 3.12 (bs, 2H), 1.48-1.24 (m, 12H), 0.88 (d, 6H, J=6.6 Hz). Electrospray MS M−1 ion=370, 372.

Step 5

3-Bromo-4-(3-bromo-5-cyano-pyridin-2-yloxy)-benzyl]-(3-methyl-butyl)-carbamic acid tert-butyl ester

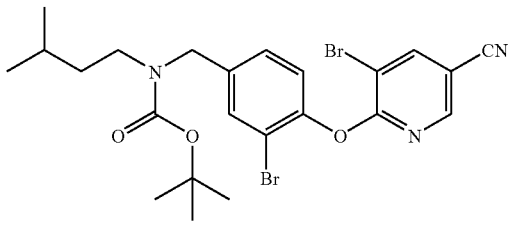

Heat a mixture of the phenol obtained in step 4 (677 mg, 1.82 mmol), 5-Bromo-6-chloro-nicotinonitrile (395 mg, 1.82 mmol), K$_2$CO$_3$ (277 mg, 2.0 mmol) and DMF (22 mL) at 100° C. under N$_2$ atmosphere overnight. Cool at room temperature. Pour into ice-water and extract with EtOAc. Dry the organic layer over Na$_2$SO$_4$. Eliminate the solvent. Purify by flash chromatography on silica gel (eluent: hexane/EtOAc 8/1) to afford the title compound (860 mg, 85%). $^1$H-NMR (CDCl$_3$, 300 MHz): 8.30 (d, 1H, J=2.0 Hz), 8.19 (d, 1H, J=2.0 Hz), 7.53 (s, 1H), 7.29 (m, 1H), 7.18 (d, 1H, J=8.3 Hz), 4.43 (m, 2H), 3.19 (m, 2H), 1.58-1.42 (m, 12H), 0.90 (d, 6H, J=6.5 Hz).

Step 6

[4-(5-Cyano-3-vinyl-pyridin-2-yloxy)-3-vinyl-benzyl]-(3-methyl-butyl)-carbamic acid tert-butyl ester

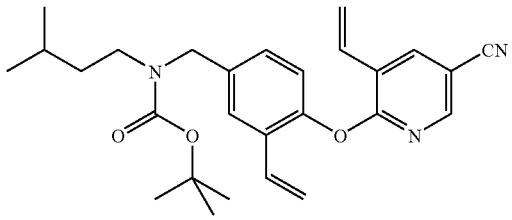

Heat a mixture of the intermediate above (154 mg, 0.28 mmol), PdCl$_2$(dppf) (23 mg), tributyl-vinyl-stannane (1.67 mmol) in dry DMF under N$_2$ atmosphere at 125° C. for 5 hours. Cool at room temperature. Filtrate over celite with EtOAc. Wash the organic layer with saturated NaCl and then saturated potassium fluoride (KF). Dry the organic layer over Na$_2$SO$_4$. Eliminate the solvent. Purify by flash chromatography on silica gel (eluent: hexane/EtOAc 40/1, 20/1 and 10/1) to afford the title compound (70 mg, 58%). $^1$H-NMR (CDCl$_3$, 300 MHz): 8.25 (d, 1H, J=2.0 Hz), 8.02 (d, 1H, J=2.4 Hz), 7.49 (bs, 1H), 7.19 (bs, 1H), 7.07-6.97 (m, 2H), 6.64 (dd, 1H, J=10.9 and 17.8 Hz), 6.01 (d, 1H, J=1.74 Hz), 5.72 (dd, 1H, J=0.8 and 17.8 Hz), 5.61 (d, 1H, J=11.3 Hz), 5.23 (d, 1H, J=11.7 Hz), 4.44 (bs, 2H), 3.1 (bs, 2H), 1.48 (bs, 12H), 0.89 (d, 6H, J=6.5 Hz). Electrospray MS M+1-$^t$Bu ion=392.

Step 7

(2-Cyano-5-oxa-4-aza-dibenzo[a,d]cyclohepten-8-ylmethyl)-(3-methyl-butyl)-carbamic acid tert-butyl ester

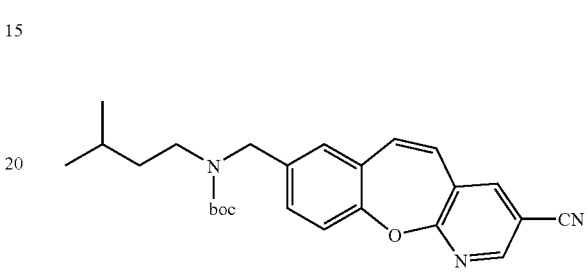

Dissolve intermediate above (142 mg, 0.32 mmol) in 1,2-DCE (previously dried over molecular sieves 3A, 33 mL), add Grubb's 2$^{nd}$ generation catalyst (54 mg, 0.06 mol). Heat the mixture under N$_2$ atmosphere at 82° C. during 6 hours. Cool at room temperature. Eliminate the solvent. Purify the by ISCO chromatography (eluent: hexane/EtOAc 8%-20%) to afford the title compound (60 mg, 46%). $^1$H-NMR (CDCl$_3$, 300 MHz): 8.53 (d, 1H, J=2.0 Hz), 7.78 (d, 1H, J=2.0 Hz), 7.31-7.17 (m, 2H), 7.06 (bs, 1H), 6.82 (d, 1H, J=11.5 Hz), 6.53 (d, 1H, J=11.3 Hz), 4.37 (s, 2H), 3.13 (bs, 2H), 1.49-1.37 (bs, 12H), 0.88 (d, 6H, J=6.5 Hz). Electrospray MS M+1 ion=420.

Step 8

(2-Carbamoyl-5-oxa-4-aza-dibenzo[a,d]cyclohepten-8-ylmethyl)-(3-methyl-butyl)-carbamic acid tert-butyl ester

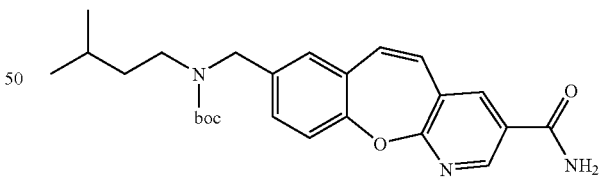

To a solution of the intermediate above (50 mg, 0.12 mmol) in dry DMSO (1.5 mL) add K$_2$CO$_3$ (8.2 mg, 0.06 mmol), cool the mixture at 0° C. and add H$_2$O$_2$ 33% (0.48 mmol) dropwise. Stir the mixture at room temperature overnight. Pour into ice-water and extract with EtOAc, dry the organic layer over Na$_2$SO$_4$. Eliminate the solvent at reduced pressure. Purify by ISCO chromatography (eluent: EtOAc) to obtain the title compound (39 mg, 78%). $^1$H-NMR (MeOD, 300 MHz): 8.53 (d, 1H, J=2.0 Hz), 7.78 (d, 1H, J=2.0 Hz), 7.31-7.17 (m, 2H), 7.06 (bs, 1H), 6.82 (d, 1H, J=11.5 Hz), 6.53 (d, 1H, J=11.3 Hz), 4.37 (s, 2H), 3.13 (bs, 2H), 1.49-1.37 (bs, 12H), 0.88 (d, 6H, J=6.5 Hz).

Step 9

(2-Carbamoyl-10,11-dihydro-5-oxa-4-aza-dibenzo[a,d]cyclohepten-8-ylmethyl)-(3-methyl-butyl)-carbamic acid tert-butyl ester

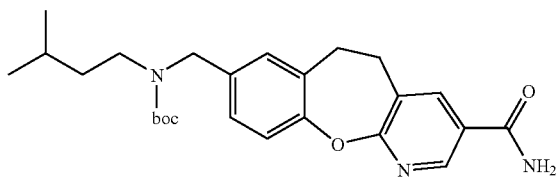

Stir a mixture of the intermediate from Step 8 Example 35 (38 mg, 0.09 mmol) and Pd/C 10% (4 mg) under $H_2$ atmosphere (1 atm) during 48 h. Filter over celite with MeOH. Eliminate the solvent to afford the title compound (35 mg, 92%). $^1$H-NMR (MeOD, 300 MHz): 8.62 (m, 1H), 8.17 (m, 1H), 7.26-7.13 (m, 3H), 4.42 (s, 2H), 3.24 (m, 2H), 3.18 (bs, 4H), 1.51-1.38 (m, 12H), 0.89 (d, 6H, J=6.5 Hz).

Step 10

8-[(3-Methyl-butylamino)-methyl]-10,11-dihydro-5-oxa-4-aza-dibenzo[a,d]cycloheptene-2-carboxylic acid amide

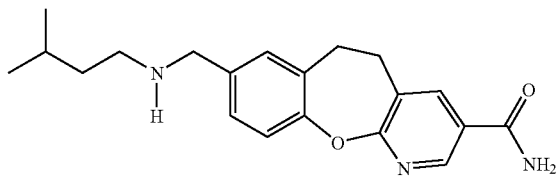

Dissolve the intermediate from step 10 above (30 mg, 0.07 mmol) in $CH_2Cl_2$ (1.5 mL). Add trifluoroacetic acid (1.82 mmol) and sir the mixture at room temperature overnight. Eliminate the solvent. Submit the crude to a SCX ion-exchange chromatography to afford a yellow oil. Purify by HPLC (basic conditions with Ammonium Bicarbonate (10 mM) at pH 8. Isocratic mode: 27% $CH_3CN$) to afford the title compound (20 mg, 67%). $^1$H-NMR (MeOD, 300 MHz): 8.61 (d, 1H, J=1.9 Hz), 8.17 (d, 1H, J=2.0 Hz), 7.28-7.26 (m, 3H), 3.80 (s, 2H), 3.19 (s, 4H), 2.70-2.65 (m, 2H), 1.70-1.57 (m, 1H), 1.50-1.43 (q, 2H, J=6.8 Hz), 0.92 (d, 6H, J=6.7 Hz). Electrospray MS M+1 ion=340.

Example 37

8-[(3-Methyl-butylamino)-methyl]-5-oxa-4-aza-dibenzo[a,d]cycloheptene-2-carboxylic acid amide

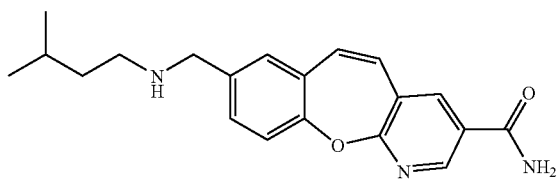

Dissolve the intermediate obtained in step 8 of example 36 (9 mg) in $CH_2Cl_2$ (1 mL). Add trifluoroacetic acid (50 μl) and stir the mixture at room temperature overnight. Eliminate the solvent. Purify by flash chromatography (eluent: eluent: $CHCl_3$/B 10%; B: $EtOH/NH_4OH$ 10%) to afford the title compound (3.5 mg, 51%). $^1$H-NMR (MeOD, 300 MHz): 8.70 (d, 1H, J=2.2 Hz), 8.20 (d, 1H, J=2.2 Hz), 7.42-7.27 (m, 3H), 6.91 (d, 1H, J=11.3 Hz), 6.75 (d, 1H, J=11.4 Hz), 3.78 (s, 2H), 2.66-2.61 (m, 2H), 1.69-1.56 (m, 1H), 1.45 (q, 2H, J=6.8 Hz), 0.91 (d, 6H, J=6.7 Hz). Electrospray MS M+1 ion=338.

The invention claimed is:

1. A compound of formula (I)

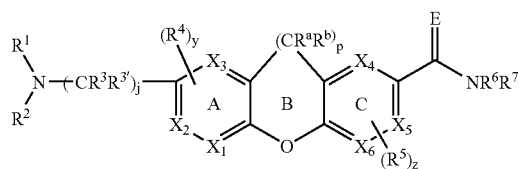

wherein:

j is 1 or 2;

y is 0, 1, or 2; and z is 0, 1, or 2;

p is 0, 1, or 2;

E is O or NH; and wherein each of $X_1$, $X_2$, $X_3$, $X_4$, $X_5$, or $X_6$, is C, CH, or N; provided that each of rings A or C has no more than 2 nitrogen atoms; and provided that Ring B has 0 or 1 double bond excluding tautomeric bonds from rings A and C;

$R^1$ and $R^2$ are independently selected from hydrogen, methyl, ethyl, propyl, isopropyl, 2-methylpentyl, t-butyl, cyclopropyl, phenyl,

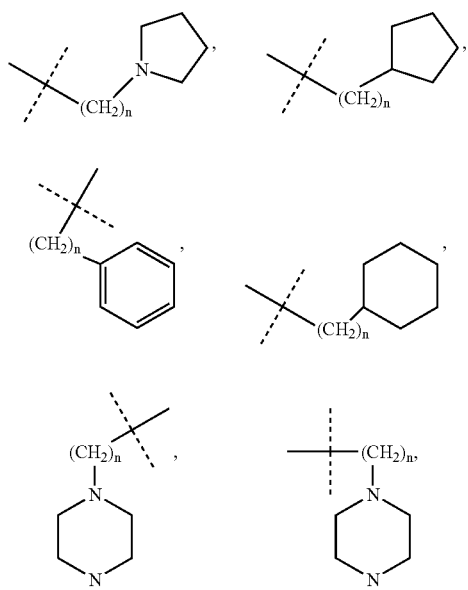

-continued

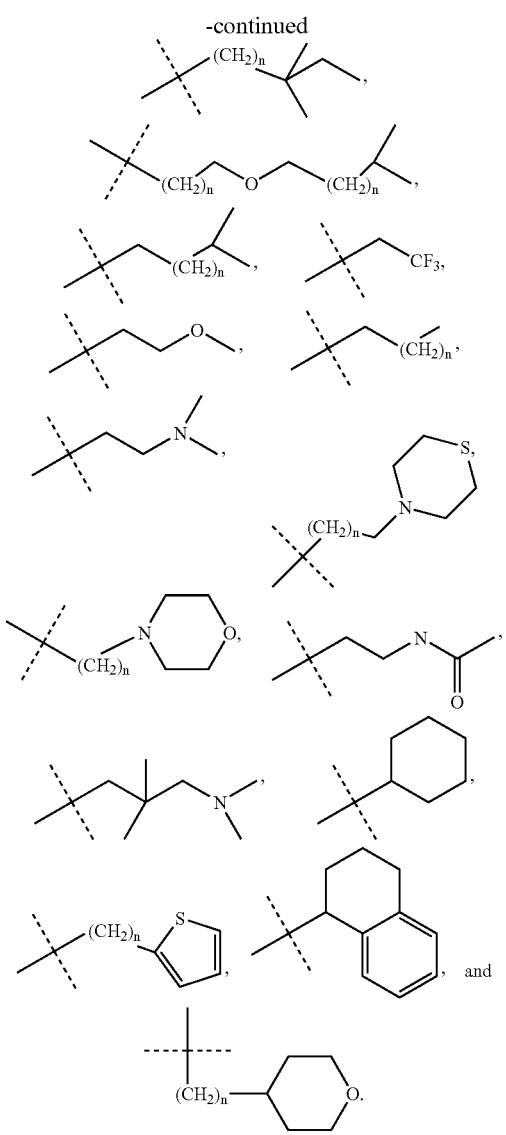

and wherein R¹ and R² may optionally combine with each other to form a 4, 5, 6, or 7-membered nitrogen-containing heterocycle which nitrogen-containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, C(O) $C_1$-$C_8$ alkyl, CO(O)$C_1$-$C_8$ alkyl, halo, $C_1$-$C_8$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^a$ and $R^b$ are each independently selected from hydrogen, and $C_1$-$C_3$ alkyl or combine with their respective carbon atoms to form the vinyl diradical —CH═CH—;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_m NSO_2 C_1$-$C_8$ alkyl, $(CH_2)_m NSO_2$phenyl, $(CH_2)_m NSO_2$aryl, —C(O)$C_1$-$C_8$ alkyl, and —C(O)O$C_1$-$C_8$ alkyl;

wherein each $R^4$ and $R^5$ is attached to its respective ring only at carbon atoms; wherein m is 1 or 2; and n is 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, C(O)$C_1$-$C_8$ alkyl, $SO_2 C_1$-$C_8$ alkyl, $SO_2 C_1$-$C_8$ alkylaryl, $SO_2 C_1$-$C_8$ alkylheterocyclic, aryl, $C_1$-$C_8$ alkylaryl, $C_3$-$C_7$ cycloalkane, $C_1$-$C_6$ alkylcycloalkane, $(CH_2)_n C(O)OR^8$, $(CH_2)_n C(O)R^8$, $(CH_2)_m C(O)NR^1 R^8$, and $(CH_2)_m NSO_2 R^8$; wherein each of the alkyl, alkenyl, and aryl groups are optionally substituted with one to five groups independently selected from $C_1$-$C_8$ alkyl, $C_2$-$C_8$ alkenyl, phenyl, and $C_1$-$C_8$ alkylaryl; and wherein $R^6$ and $R^7$ may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl;

or a compound selected from 8-cyclooctylaminomethyl-10,11-dihydro-dibenzo[b,f]oxepine-2-carboxylic acid amide; 8-cycloheptylaminomethyl-10,11-dihydro-dibenzo[b,f]oxepine-2-carboxylic acid amide; 8-[(cycloheptylmethyl-amino)-methyl]-10,11-dihydro-dibenzo[b,f]oxepine-2-carboxylic acid amide; 8-{[cyclopropylmethyl-(3-methyl-butyl)-amino]-methyl}-10,11-dihydro-dibenzo[b,f]oxepine-2-carboxylic acid amide; 8-[2-(4-chloro-phenyl)-pyrrolidin-1-ylmethyl]-10,11-dihydro-dibenzo[b,f]oxepine-2-carboxylic acid amide;

8-(2-phenyl-azepan-1-ylmethyl)-10,11-dihydro-dibenzo[b,f]oxepine-2-carboxylic acid amide;

and 8-(2-benzyl-pyrrolidin-1-ylmethyl)-10,11-dihydro-dibenzo[b,f]oxepine-2-carboxylic acid amide;

or a pharmaceutically acceptable salt or solvate thereof.

2. The compound according to claim 1 wherein the A-ring is selected from the group consisting of phenyl, pyridine, pyrimidine and pyrazine.

3. A compound according to claim 1 wherein the C-ring is selected from the group consisting of phenyl and pyridine.

4. A compound according to claim 1 wherein the A-ring is phenyl and the C ring is pyridine.

5. A compound according to claim 1 wherein both A and C rings are phenyl.

6. A compound according to claim 1 wherein p is 2 and both $R^a$ and $R^b$ are hydrogen.

7. A compound according to claim 1 wherein $(CR^a R^b)_p$— is —CH═CH—.

8. A compound according to claim 1 wherein E is an oxygen atom.

9. A compound according to claim 1 wherein y is 0 or 1, and $R^4$ is independently selected from the group consisting of fluoro, chloro, bromo, methoxy, ethoxy, methyl, ethyl, isopropyl, trifluoromethyl, phenyl, benzyl and ethoxy.

10. A compound according to claim 1 wherein z is 0 or 1, and $R^5$ is independently selected from the group consisting of fluoro, chloro, bromo, methoxy, ethoxy, methyl, ethyl, isopropyl, trifluoromethyl, phenyl, and benzyl.

11. The compound according to claim 1 wherein $R^6$ and $R^7$ are each independently selected from the group consisting of hydrogen, methyl, ethyl, propyl, isopropyl, and phenyl.

12. A compound according to claim 1 wherein E is an oxygen atom, wherein both $R^6$ and $R^7$ are hydrogen atoms.

13. A compound selected from the group consisting of:
8-[(3-Methyl-butylamino)-methyl]-10,11-dihydro-dibenzo[b,f]oxepine-2-carboxylic acid amide, 8-(Isobutylamino-methyl)-10,11-dihydro-dibenzo[b,f]ox-epine-2-carboxylic acid amide,
8-[(4-Methyl-pentylamino)-methyl]-10,11-dihydro-dibenzo[b,f]oxepine-2-carboxylic acid amide,
8-[(2-Thiophen-2-yl-ethylamino)-methyl]-10,11-dihydro-dibenzo[b,f]oxepine-2-carboxylic acid amide,
8-Pentylaminomethyl-10,11-dihydro-dibenzo[b,f]ox-epine-2-carboxylic acid amide,
8-Hexylaminomethyl-10,11-dihydro-dibenzo[b,f]ox-epine-2-carboxylic acid amide,
8-[(Cyclohexylmethyl-amino)-methyl]-10,11-dihydro-dibenzo[b,f]oxepine-2-carboxylic acid amide,
8-Cyclooctylaminomethyl-10,11-dihydro-dibenzo[b,f]oxepine-2-carboxylic acid amide,
8-Cycloheptylaminomethyl-10,11-dihydro-dibenzo[b,f]oxepine-2-carboxylic acid amide,
8-[(Cycloheptylmethyl-amino)-methyl]-10,11-dihydro-dibenzo[b,f]oxepine-2-carboxylic acid amide trifluoroacetate salt,
8-{[2-(Tetrahydro-pyran-4-yl)-ethylamino]-methyl}-10,11-dihydro-dibenzo[b,f]oxepine-2-carboxylic acid amide,
8-[(3,3-Dimethyl-butylamino)-methyl]-10,11-dihydro-dibenzo[b,f]oxepine-2-carboxylic acid amide,
8-[(2-Cyclopentyl-ethylamino)-methyl]-10,11-dihydro-dibenzo[b,f]oxepine-2-carboxylic acid amide,
8-[(3-Morpholin-4-yl-propylamino)-methyl]-10,11-dihydro-dibenzo[b,f]oxepine-2-carboxylic acid amide,
8-[(3-Ethoxy-propylamino)-methyl]-10,11-dihydro-dibenzo[b,f]oxepine-2-carboxylic acid amide,
8-[(2-Diethylamino-ethylamino)-methyl]-10,11-dihydro-dibenzo[b,f]oxepine-2-carboxylic acid amide,
8-[(3-Methoxy-propylamino)-methyl]-10,11-dihydro-dibenzo[b,f]oxepine-2-carboxylic acid amide, and
8-[(3-Phenyl-propylamino)-methyl]-10,11-dihydro-dibenzo[b,f]oxepine-2-carboxylic acid amide,
8-(3-Phenyl-pyrrolidin-1-ylmethyl)-10,11-dihydro-dibenzo[b,f]oxepine-2-carboxylic acid amide,
8-(3-Phenyl-piperidin-1-ylmethyl)-10,11-dihydro-dibenzo[b,f]oxepine-2-carboxylic acid amide,
8-[2-(4-Chloro-phenyl)-pyrrolidin-1-ylmethyl]-10,11-dihydro-dibenzo[b,f]oxepine-2-carboxylic acid amide,
8-(2-Phenyl-pyrrolidin-1-ylmethyl)-10,11-dihydro-dibenzo[b,f]oxepine-2-carboxylic acid amide,
8-(2-Phenyl-piperidin-1-ylmethyl)-10,11-dihydro-dibenzo[b,f]oxepine-2-carboxylic acid amide,
8-(2-Phenyl-azepan-1-ylmethyl)-10,11-dihydro-dibenzo[b,f]oxepine-2-carboxylic acid amide,
8-(2-Benzyl-pyrrolidin-1-ylmethyl)-10,11-dihydro-dibenzo[b,f]oxepine-2-carboxylic acid amide,
8-[(3-Methyl-butylamino)-methyl]-dibenzofuran-2-carboxylic acid amide,
8-[(3-Methyl-butylamino)-methyl]-10,11-dihydro-dibenzo[b,j]oxepine-2-carboxilic acid amide,
8-[(3-Methyl-butylamino)-methyl]-10,11-dihydro-5-oxa-4-aza-dibenzo[a,d]cycloheptene-2-carboxylic acid amide,
8-[(3-Methyl-butylamino)-methyl]-5-oxa-4-aza-dibenzo[a,d]cycloheptene-2-carboxylic acid amide,
or a pharmaceutically acceptable salt or solvate thereof.

14. A pharmaceutical composition comprising a therapeutically effective amount of a compound of claim 1, or a pharmaceutically acceptable salt or solvate thereof in association with a carrier, diluent and/or excipient.

\* \* \* \* \*

UNITED STATES PATENT AND TRADEMARK OFFICE
CERTIFICATE OF CORRECTION

PATENT NO. : 7,288,543 B2  Page 1 of 1
APPLICATION NO. : 10/598690
DATED : October 30, 2007
INVENTOR(S) : Howard Barff Broughton et al.

It is certified that error appears in the above-identified patent and that said Letters Patent is hereby corrected as shown below:

On the Title Page:
Insert --(60) Related U.S. Application Data
Provisional Application No. 60/553,187 filed March 15, 2004--.

Col. 1, line 2 of the specification, insert the following cross-reference after the title:
--This application is the national phase application, under 35 USC 371, for PCT/US2005/007052, filed March 8, 2005, which claims the benefit, under 35 USC 119(e), of EP application 04380057.2, filed March 12, 2004, and US provisional application no. 60/553,187, filed March 15, 2004.--.

Signed and Sealed this

Thirtieth Day of November, 2010

David J. Kappos
*Director of the United States Patent and Trademark Office*